(12) United States Patent
Odom

(10) Patent No.: US 7,776,037 B2
(45) Date of Patent: *Aug. 17, 2010

(54) SYSTEM AND METHOD FOR CONTROLLING ELECTRODE GAP DURING TISSUE SEALING

(75) Inventor: Darren Odom, Longmont, CO (US)

(73) Assignee: Covidien AG, Neuhausen am Rheinfall (CH)

( * ) Notice: Subject to any disclaimer, the term of this patent is extended or adjusted under 35 U.S.C. 154(b) by 891 days.

This patent is subject to a terminal disclaimer.

(21) Appl. No.: 11/482,886

(22) Filed: Jul. 7, 2006

(65) Prior Publication Data

US 2008/0009860 A1  Jan. 10, 2008

(51) Int. Cl.
*A61B 18/18* (2006.01)
(52) U.S. Cl. .......................... 606/51; 606/52
(58) Field of Classification Search ............. 606/50–52, 606/205–207
See application file for complete search history.

(56) References Cited

U.S. PATENT DOCUMENTS

| | | |
|---|---|---|
| 371,664 A | 10/1887 | Brannan et al. |
| 702,472 A | 6/1902 | Pignolet |
| 728,883 A | 5/1903 | Downes |
| 1,586,645 A | 6/1926 | Bierman |
| 1,813,902 A | 7/1931 | Bovie |
| 1,822,330 A | 9/1931 | Ainslie |
| 1,852,542 A | 4/1932 | Sovatkin |
| 2,002,594 A | 5/1935 | Wappler et al. |
| 2,011,169 A | 8/1935 | Wappler |
| 2,031,682 A | 2/1936 | Wappler et al. |
| 2,054,149 A | 9/1936 | Wappler |
| 2,176,479 A | 10/1939 | Willis |
| 2,305,156 A | 4/1941 | Grubel |
| 2,279,753 A | 4/1942 | Knopp |

(Continued)

FOREIGN PATENT DOCUMENTS

CA    2104423    2/1994

(Continued)

OTHER PUBLICATIONS

Int'l Search Report EP 05016399 dated Jan. 5, 2006.

(Continued)

*Primary Examiner*—Michael Peffley
*Assistant Examiner*—Samantha Muro

(57) ABSTRACT

An electrosurgical system for sealing tissue is disclosed that includes an electrosurgical forceps. The forceps includes a drive rod and an end effector assembly coupled to the drive rod at a distal end thereof. The end effector assembly includes jaw members wherein longitudinal reciprocation of the drive rod moves the jaw members from a first position in spaced relation relative to one another to a subsequent position wherein the jaw members cooperate to grasp tissue therebetween. Each of the jaw members includes a sealing plate that communicates electrosurgical energy through tissue held therebetween. The jaw members are adapted to connect to an electrosurgical generator. The system also includes one or more sensors that determine a gap distance between the sealing plates of the jaw members and a pressure applicator coupled to the drive rod. The pressure applicator is configured to move the drive rod in a longitudinal direction. The system further includes a controller adapted to communicate with the sensors and to control the pressure applicator in response to the determined gap distance during the sealing process.

8 Claims, 9 Drawing Sheets

U.S. PATENT DOCUMENTS

| | | |
|---|---|---|
| 2,327,353 A | 8/1943 | Karle |
| 2,632,661 A | 8/1948 | Cristofv |
| 2,668,538 A | 2/1954 | Baker |
| 2,796,065 A | 6/1957 | Kapp |
| 3,073,311 A | 1/1963 | Tibbs et al. |
| 3,372,288 A | 3/1968 | Wigington |
| 3,459,187 A | 8/1969 | Pallotta |
| 3,643,663 A | 2/1972 | Sutter |
| 3,648,001 A | 3/1972 | Anderson et al. |
| 3,651,811 A | 3/1972 | Hildebrandt et al. |
| 3,678,229 A | 7/1972 | Osika |
| 3,720,896 A | 3/1973 | Beierlein |
| 3,763,726 A | 10/1973 | Hildebrand |
| 3,779,918 A | 12/1973 | Ikeda et al. |
| 3,801,766 A | 4/1974 | Morrison, Jr. |
| 3,862,630 A | 1/1975 | Balamuth |
| 3,863,339 A | 2/1975 | Reaney et al. |
| 3,866,610 A | 2/1975 | Kletschka |
| 3,911,766 A | 10/1975 | Fridolph et al. |
| 3,920,021 A | 11/1975 | Hiltebrandt |
| 3,921,641 A | 11/1975 | Hulka |
| 3,938,527 A | 2/1976 | Rioux et al. |
| 3,952,749 A | 4/1976 | Fridolph et al. |
| 3,970,088 A | 7/1976 | Morrison |
| 3,987,795 A | 10/1976 | Morrison |
| 4,005,714 A | 2/1977 | Hiltebrandt |
| 4,016,881 A | 4/1977 | Rioux et al. |
| 4,041,952 A | 8/1977 | Morrison, Jr. et al. |
| 4,043,342 A | 8/1977 | Morrison, Jr. |
| 4,074,718 A | 2/1978 | Morrison, Jr. |
| 4,076,028 A | 2/1978 | Simmons |
| 4,080,820 A | 3/1978 | Allen |
| 4,088,134 A | 5/1978 | Mazzariello |
| 4,112,950 A | 9/1978 | Pike |
| 4,127,222 A | 11/1978 | Adams |
| 4,128,099 A | 12/1978 | Bauer |
| 4,165,746 A | 8/1979 | Burgin |
| 4,187,420 A | 2/1980 | Piber |
| 4,233,734 A | 11/1980 | Bies |
| 4,236,470 A | 12/1980 | Stenson |
| 4,300,564 A | 11/1981 | Furihata |
| 4,311,145 A | 1/1982 | Esty et al. |
| D263,020 S | 2/1982 | Rau, III |
| 4,370,980 A | 2/1983 | Lottick |
| 4,375,218 A | 3/1983 | DiGeronimo |
| 4,416,276 A | 11/1983 | Newton et al. |
| 4,418,692 A | 12/1983 | Guay |
| 4,443,935 A | 4/1984 | Zamba et al. |
| 4,452,246 A | 6/1984 | Bader et al. |
| 4,470,786 A | 9/1984 | Sano et al. |
| 4,492,231 A | 1/1985 | Auth |
| 4,493,320 A | 1/1985 | Treat |
| 4,503,855 A | 3/1985 | Maslanka |
| 4,506,669 A | 3/1985 | Blake, III |
| 4,509,518 A | 4/1985 | McGarry et al. |
| 4,552,143 A | 11/1985 | Lottick |
| 4,574,804 A | 3/1986 | Kurwa |
| 4,597,379 A | 7/1986 | Kihn et al. |
| 4,600,007 A | 7/1986 | Lahodny et al. |
| 4,624,254 A | 11/1986 | McGarry et al. |
| 4,655,215 A | 4/1987 | Pike |
| 4,655,216 A | 4/1987 | Tischer |
| 4,657,016 A | 4/1987 | Garito et al. |
| 4,662,372 A | 5/1987 | Sharkany et al. |
| 4,671,274 A | 6/1987 | Sorochenko |
| 4,685,459 A | 8/1987 | Koch et al. |
| 4,733,662 A | 3/1988 | DeSatnick et al. |
| D295,893 S | 5/1988 | Sharkany et al. |
| D295,894 S | 5/1988 | Sharkany et al. |
| 4,754,892 A | 7/1988 | Retief |
| 4,763,669 A | 8/1988 | Jaeger |
| 4,827,929 A | 5/1989 | Hodge |
| 4,829,313 A | 5/1989 | Taggart |
| 4,846,171 A | 7/1989 | Kauphusman et al. |
| 4,887,612 A | 12/1989 | Esser et al. |
| 4,938,761 A | 7/1990 | Ensslin |
| 4,947,009 A | 8/1990 | Osika et al. |
| 4,985,030 A | 1/1991 | Melzer et al. |
| 5,007,908 A | 4/1991 | Rydell |
| 5,026,370 A | 6/1991 | Lottick |
| 5,026,371 A | 6/1991 | Rydell et al. |
| 5,035,695 A | 7/1991 | Weber, Jr. et al. |
| 5,037,433 A | 8/1991 | Wilk et al. |
| 5,042,707 A | 8/1991 | Taheri |
| 5,047,046 A | 9/1991 | Bodoia |
| 5,078,716 A | 1/1992 | Doll |
| 5,084,057 A | 1/1992 | Green et al. |
| 5,085,659 A | 2/1992 | Rydell |
| 5,099,840 A | 3/1992 | Goble et al. |
| 5,100,430 A | 3/1992 | Avellanet et al. |
| 5,108,392 A | 4/1992 | Spingler |
| 5,112,343 A | 5/1992 | Thornton |
| 5,116,332 A | 5/1992 | Lottick |
| 5,147,357 A | 9/1992 | Rose et al. |
| 5,151,102 A | 9/1992 | Kamiyama et al. |
| 5,151,978 A | 9/1992 | Bronikowski et al. |
| 5,176,695 A | 1/1993 | Dulebohn |
| 5,190,541 A | 3/1993 | Abele et al. |
| 5,196,009 A | 3/1993 | Kirwan, Jr. |
| 5,197,964 A | 3/1993 | Parins |
| 5,209,747 A | 5/1993 | Knoepfler |
| 5,211,655 A | 5/1993 | Hasson |
| 5,215,101 A | 6/1993 | Jacobs et al. |
| 5,217,457 A | 6/1993 | Delahuerga et al. |
| 5,217,458 A | 6/1993 | Parins |
| 5,217,460 A | 6/1993 | Knoepfler |
| 5,219,354 A | 6/1993 | Choudhury et al. |
| 5,244,462 A | 9/1993 | Delahuerga et al. |
| 5,250,047 A | 10/1993 | Rydell |
| 5,250,063 A | 10/1993 | Abidin et al. |
| 5,258,001 A | 11/1993 | Corman |
| 5,258,006 A | 11/1993 | Rydell et al. |
| 5,261,918 A | 11/1993 | Phillips et al. |
| 5,275,615 A | 1/1994 | Rose |
| 5,277,201 A | 1/1994 | Stern |
| 5,282,799 A | 2/1994 | Rydell |
| 5,282,800 A | 2/1994 | Foshee et al. |
| 5,282,826 A | 2/1994 | Quadri |
| 5,290,286 A | 3/1994 | Parins |
| 5,300,082 A | 4/1994 | Sharpe et al. |
| 5,304,203 A | 4/1994 | El-Mallawany et al. |
| 5,308,353 A | 5/1994 | Beurrier |
| 5,308,357 A | 5/1994 | Lichtman |
| 5,313,027 A | 5/1994 | Inoue et al. |
| 5,314,445 A | 5/1994 | Degwitz et al. |
| 5,318,589 A | 6/1994 | Lichtman |
| 5,324,289 A | 6/1994 | Eggers |
| D348,930 S | 7/1994 | Olson |
| 5,326,806 A | 7/1994 | Yokoshima et al. |
| 5,330,471 A | 7/1994 | Eggers |
| 5,330,502 A | 7/1994 | Hassler et al. |
| 5,334,183 A | 8/1994 | Wuchinich |
| 5,334,215 A | 8/1994 | Chen |
| 5,336,220 A | 8/1994 | Ryan et al. |
| 5,336,221 A | 8/1994 | Anderson |
| 5,342,359 A | 8/1994 | Rydell |
| 5,342,381 A | 8/1994 | Tidemand |
| 5,342,393 A | 8/1994 | Stack |
| 5,344,424 A | 9/1994 | Roberts et al. |
| 5,350,391 A | 9/1994 | Iacovelli |
| 5,352,222 A | 10/1994 | Rydell |
| 5,354,271 A | 10/1994 | Voda |
| 5,356,408 A | 10/1994 | Rydell |
| 5,366,477 A | 11/1994 | LeMarie, III et al. |

| | | | | | |
|---|---|---|---|---|---|
| 5,368,600 A | 11/1994 | Failla et al. | 5,569,241 A | 10/1996 | Edwards |
| 5,374,277 A | 12/1994 | Hassler | 5,569,243 A | 10/1996 | Kortenbach et al. |
| 5,376,089 A | 12/1994 | Smith | 5,571,100 A | 11/1996 | Goble et al. |
| 5,383,875 A | 1/1995 | Bays et al. | 5,573,424 A | 11/1996 | Poppe |
| 5,383,897 A | 1/1995 | Wholey | 5,573,534 A | 11/1996 | Stone |
| 5,389,098 A | 2/1995 | Tsuruta et al. | 5,573,535 A | 11/1996 | Viklund |
| 5,389,103 A | 2/1995 | Melzer et al. | 5,575,799 A | 11/1996 | Bolanos et al. |
| 5,389,104 A | 2/1995 | Hahnen et al. | 5,575,805 A | 11/1996 | Li |
| 5,391,166 A | 2/1995 | Eggers | 5,578,052 A | 11/1996 | Koros et al. |
| 5,391,183 A | 2/1995 | Janzen et al. | 5,579,781 A | 12/1996 | Cooke |
| 5,396,900 A | 3/1995 | Slater et al. | 5,582,611 A | 12/1996 | Tsukagoshi et al. |
| 5,403,312 A | 4/1995 | Yates et al. | 5,582,617 A | 12/1996 | Klieman et al. |
| 5,403,342 A | 4/1995 | Tovey et al. | 5,585,896 A | 12/1996 | Yamazaki et al. |
| 5,405,344 A | 4/1995 | Williamson et al. | 5,590,570 A | 1/1997 | LeMaire, III et al. |
| 5,409,763 A | 4/1995 | Serizawa et al. | 5,591,181 A | 1/1997 | Stone et al. |
| 5,411,519 A | 5/1995 | Tovey et al. | 5,597,107 A | 1/1997 | Knodel et al. |
| 5,411,520 A | 5/1995 | Nash et al. | 5,601,224 A | 2/1997 | Bishop et al. |
| 5,413,571 A | 5/1995 | Katsaros et al. | 5,601,601 A | 2/1997 | Tal et al. |
| 5,415,656 A | 5/1995 | Tihon et al. | 5,601,641 A | 2/1997 | Stephens |
| 5,415,657 A | 5/1995 | Taymor-Luria | 5,603,711 A | 2/1997 | Parins et al. |
| 5,422,567 A | 6/1995 | Matsunaga | 5,603,723 A | 2/1997 | Aranyi et al. |
| 5,423,810 A | 6/1995 | Goble et al. | 5,611,798 A | 3/1997 | Eggers |
| 5,425,690 A | 6/1995 | Chang | 5,611,808 A | 3/1997 | Hossain et al. |
| 5,425,739 A | 6/1995 | Jessen | 5,611,813 A | 3/1997 | Lichtman |
| 5,429,616 A | 7/1995 | Schaffer | 5,620,415 A | 4/1997 | Lucey et al. |
| 5,431,672 A | 7/1995 | Cote et al. | 5,620,453 A | 4/1997 | Nallakrishnan |
| 5,431,674 A | 7/1995 | Basile et al. | 5,620,459 A | 4/1997 | Lichtman |
| 5,437,292 A | 8/1995 | Kipshidze et al. | 5,624,452 A | 4/1997 | Yates |
| 5,438,302 A | 8/1995 | Goble | 5,626,578 A | 5/1997 | Tihon |
| 5,439,478 A | 8/1995 | Palmer | 5,626,609 A | 5/1997 | Zvenyatsky et al. |
| 5,441,517 A | 8/1995 | Kensey et al. | 5,630,833 A | 5/1997 | Katsaros et al. |
| 5,443,463 A | 8/1995 | Stern et al. | 5,637,110 A | 6/1997 | Pennybacker et al. |
| 5,443,464 A | 8/1995 | Russell et al. | 5,638,003 A | 6/1997 | Hall |
| 5,443,480 A | 8/1995 | Jacobs et al. | 5,643,294 A | 7/1997 | Tovey et al. |
| 5,445,638 A | 8/1995 | Rydell et al. | 5,647,869 A | 7/1997 | Goble et al. |
| 5,445,658 A | 8/1995 | Durrfeld et al. | 5,647,871 A | 7/1997 | Levine et al. |
| 5,449,480 A | 9/1995 | Kuriya et al. | 5,649,959 A | 7/1997 | Hannam et al. |
| 5,451,224 A | 9/1995 | Goble et al. | 5,655,650 A | 8/1997 | Naitou |
| 5,454,823 A | 10/1995 | Richardson et al. | 5,658,281 A | 8/1997 | Heard |
| 5,454,827 A | 10/1995 | Aust et al. | D384,413 S | 9/1997 | Zlock et al. |
| 5,456,684 A | 10/1995 | Schmidt et al. | 5,662,667 A | 9/1997 | Knodel |
| 5,458,598 A | 10/1995 | Feinberg et al. | 5,665,100 A | 9/1997 | Yoon |
| 5,460,629 A | 10/1995 | Shlain et al. | 5,667,526 A | 9/1997 | Levin |
| 5,461,765 A | 10/1995 | Linden et al. | 5,674,220 A | 10/1997 | Fox et al. |
| 5,462,546 A | 10/1995 | Rydell | 5,674,229 A | 10/1997 | Tovey et al. |
| 5,472,442 A | 12/1995 | Klicek | 5,681,282 A | 10/1997 | Eggers et al. |
| 5,472,443 A | 12/1995 | Cordis et al. | 5,688,270 A | 11/1997 | Yates et al. |
| 5,478,351 A | 12/1995 | Meade et al. | 5,690,652 A | 11/1997 | Wurster et al. |
| 5,480,406 A | 1/1996 | Nolan et al. | 5,690,653 A | 11/1997 | Richardson et al. |
| 5,480,409 A | 1/1996 | Riza | 5,693,051 A | 12/1997 | Schulze et al. |
| 5,484,436 A | 1/1996 | Eggers et al. | 5,693,920 A | 12/1997 | Maeda |
| 5,496,312 A | 3/1996 | Klicek | 5,695,522 A | 12/1997 | LeMaire, III et al. |
| 5,496,317 A | 3/1996 | Goble et al. | 5,700,261 A | 12/1997 | Brinkerhoff |
| 5,496,347 A | 3/1996 | Hashiguchi et al. | 5,700,270 A | 12/1997 | Peyser et al. |
| 5,499,997 A | 3/1996 | Sharpe et al. | 5,702,390 A | 12/1997 | Austin et al. |
| 5,509,922 A | 4/1996 | Aranyi et al. | 5,707,369 A | 1/1998 | Vaitekunas et al. |
| 5,514,134 A | 5/1996 | Rydell et al. | 5,709,680 A | 1/1998 | Yates et al. |
| 5,527,313 A | 6/1996 | Scott et al. | 5,716,366 A | 2/1998 | Yates |
| 5,528,833 A | 6/1996 | Sakuma | 5,720,744 A | 2/1998 | Eggleston et al. |
| 5,529,067 A | 6/1996 | Larsen et al. | 5,722,421 A | 3/1998 | Francese et al. |
| 5,531,744 A | 7/1996 | Nardella et al. | 5,725,536 A | 3/1998 | Oberlin et al. |
| 5,536,251 A | 7/1996 | Evard et al. | 5,727,428 A | 3/1998 | LeMaire, III et al. |
| 5,540,684 A | 7/1996 | Hassler, Jr. | 5,735,848 A | 4/1998 | Yates et al. |
| 5,540,685 A | 7/1996 | Parins et al. | 5,743,906 A | 4/1998 | Parins et al. |
| 5,540,706 A | 7/1996 | Aust et al. | 5,752,973 A | 5/1998 | Kieturakis |
| 5,540,715 A | 7/1996 | Katsaros et al. | 5,755,717 A | 5/1998 | Yates et al. |
| 5,542,945 A | 8/1996 | Fritzsch | 5,759,188 A | 6/1998 | Yoon |
| 5,558,671 A | 9/1996 | Yates | 5,766,130 A | 6/1998 | Selmonosky |
| 5,558,672 A | 9/1996 | Edwards et al. | 5,766,166 A | 6/1998 | Hooven |
| 5,562,619 A | 10/1996 | Mirarchi et al. | 5,766,170 A | 6/1998 | Eggers |
| 5,562,699 A | 10/1996 | Heimberger et al. | 5,766,196 A | 6/1998 | Griffiths |
| 5,562,720 A | 10/1996 | Stern et al. | 5,769,849 A | 6/1998 | Eggers |
| 5,564,615 A | 10/1996 | Bishop et al. | 5,772,655 A | 6/1998 | Bauer et al. |

| | | | | | | |
|---|---|---|---|---|---|---|
| 5,772,670 | A | 6/1998 | Brosa | 5,984,939 A | 11/1999 | Yoon |
| 5,776,128 | A | 7/1998 | Eggers | 5,989,277 A | 11/1999 | LeMaire, III et al. |
| 5,776,130 | A | 7/1998 | Buysse et al. | 5,993,466 A | 11/1999 | Yoon |
| 5,779,646 | A | 7/1998 | Koblish et al. | 5,993,467 A | 11/1999 | Yoon |
| 5,779,701 | A | 7/1998 | McBrayer et al. | 5,997,565 A | 12/1999 | Inoue |
| H1745 | H | 8/1998 | Paraschac | 6,004,332 A | 12/1999 | Yoon et al. |
| 5,792,137 | A | 8/1998 | Carr et al. | 6,004,335 A | 12/1999 | Vaitekunas et al. |
| 5,792,165 | A | 8/1998 | Klieman et al. | 6,010,516 A | 1/2000 | Hulka et al. |
| 5,792,177 | A | 8/1998 | Kaseda | 6,017,358 A | 1/2000 | Yoon et al. |
| 5,797,537 | A | 8/1998 | Oberlin et al. | 6,021,693 A | 2/2000 | Feng-Sing |
| 5,797,927 | A | 8/1998 | Yoon | 6,024,741 A | 2/2000 | Williamson et al. |
| 5,797,938 | A | 8/1998 | Paraschac et al. | 6,024,743 A | 2/2000 | Edwards |
| 5,797,941 | A | 8/1998 | Schulze et al. | 6,024,744 A | 2/2000 | Kese et al. |
| 5,797,958 | A | 8/1998 | Yoon | 6,027,522 A | 2/2000 | Palmer |
| 5,800,449 | A | 9/1998 | Wales | 6,030,384 A | 2/2000 | Nezhat |
| 5,807,393 | A | 9/1998 | Williamson, IV et al. | 6,033,399 A | 3/2000 | Gines |
| 5,810,764 | A | 9/1998 | Eggers et al. | 6,039,733 A | 3/2000 | Buysse et al. |
| 5,810,805 | A | 9/1998 | Sutcu et al. | 6,041,679 A | 3/2000 | Slater et al. |
| 5,810,808 | A | 9/1998 | Eggers | 6,050,996 A | 4/2000 | Schmaltz et al. |
| 5,810,811 | A | 9/1998 | Yates et al. | 6,053,914 A | 4/2000 | Eggers et al. |
| 5,810,877 | A | 9/1998 | Roth et al. | 6,053,933 A | 4/2000 | Balazs et al. |
| 5,814,043 | A | 9/1998 | Shapeton | D424,694 S | 5/2000 | Tetzlaff et al. |
| 5,814,054 | A | 9/1998 | Kortenbach et al. | D425,201 S | 5/2000 | Tetzlaff et al. |
| 5,817,093 | A | 10/1998 | Williamson, IV et al. | 6,059,782 A | 5/2000 | Novak et al. |
| 5,817,119 | A | 10/1998 | Klieman et al. | 6,066,139 A | 5/2000 | Ryan et al. |
| 5,820,630 | A | 10/1998 | Lind | 6,074,386 A | 6/2000 | Goble et al. |
| 5,824,978 | A | 10/1998 | Karasik et al. | 6,077,287 A | 6/2000 | Taylor et al. |
| 5,827,271 | A | 10/1998 | Buysse et al. | 6,080,180 A | 6/2000 | Yoon et al. |
| 5,827,279 | A | 10/1998 | Hughett et al. | RE36,795 E | 7/2000 | Rydell |
| 5,827,281 | A | 10/1998 | Levin | 6,083,223 A | 7/2000 | Baker |
| 5,827,323 | A | 10/1998 | Klieman et al. | 6,086,586 A | 7/2000 | Hooven |
| 5,827,548 | A | 10/1998 | Lavallee et al. | 6,086,601 A | 7/2000 | Yoon |
| 5,833,690 | A | 11/1998 | Yates et al. | 6,090,107 A | 7/2000 | Borgmeier et al. |
| 5,843,080 | A | 12/1998 | Fleenor et al. | 6,096,037 A | 8/2000 | Mulier et al. |
| 5,849,022 | A | 12/1998 | Sakashita et al. | 6,099,550 A | 8/2000 | Yoon |
| 5,853,412 | A | 12/1998 | Mayenberger | 6,102,909 A | 8/2000 | Chen et al. |
| 5,859,527 | A | 1/1999 | Cook | 6,106,542 A | 8/2000 | Toybin et al. |
| 5,860,976 | A | 1/1999 | Billings et al. | 6,110,171 A | 8/2000 | Rydell |
| 5,876,401 | A | 3/1999 | Schulze et al. | 6,113,596 A | 9/2000 | Hooven et al. |
| 5,876,412 | A | 3/1999 | Piraka | 6,113,598 A | 9/2000 | Baker |
| 5,882,567 | A | 3/1999 | Cavallaro et al. | 6,117,158 A | 9/2000 | Measamer et al. |
| 5,891,141 | A | 4/1999 | Rydell | 6,122,549 A | 9/2000 | Sharkey et al. |
| 5,891,142 | A | 4/1999 | Eggers et al. | 6,123,701 A | 9/2000 | Nezhat |
| 5,893,863 | A | 4/1999 | Yoon | H1904 H | 10/2000 | Yates et al. |
| 5,893,875 | A | 4/1999 | O'Connor et al. | 6,126,658 A | 10/2000 | Baker |
| 5,893,877 | A | 4/1999 | Gampp, Jr. et al. | 6,126,665 A | 10/2000 | Yoon |
| 5,897,563 | A | 4/1999 | Yoon et al. | 6,139,563 A | 10/2000 | Cosgrove, III et al. |
| 5,902,301 | A | 5/1999 | Olig | 6,143,005 A | 11/2000 | Yoon et al. |
| 5,906,630 | A | 5/1999 | Anderhub et al. | 6,152,923 A | 11/2000 | Ryan |
| 5,908,420 | A | 6/1999 | Parins et al. | 6,162,220 A | 12/2000 | Nezhat |
| 5,908,432 | A | 6/1999 | Pan | 6,171,316 B1 | 1/2001 | Kovac et al. |
| 5,911,719 | A | 6/1999 | Eggers | 6,174,309 B1 | 1/2001 | Wrublewski et al. |
| 5,913,874 | A | 6/1999 | Berns et al. | 6,178,628 B1 | 1/2001 | Clemens et al. |
| 5,921,916 | A | 7/1999 | Aeikens et al. | 6,179,834 B1 | 1/2001 | Buysse et al. |
| 5,921,984 | A | 7/1999 | Sutcu et al. | 6,179,837 B1 | 1/2001 | Hooven |
| 5,925,043 | A | 7/1999 | Kumar et al. | 6,183,467 B1 | 2/2001 | Shapeton et al. |
| 5,928,136 | A | 7/1999 | Barry | 6,187,003 B1 | 2/2001 | Buysse et al. |
| 5,935,126 | A | 8/1999 | Riza | 6,190,386 B1 | 2/2001 | Rydell |
| 5,941,869 | A | 8/1999 | Patterson et al. | 6,190,400 B1 | 2/2001 | VanDeMoer et al. |
| 5,944,718 | A | 8/1999 | Dafforn et al. | 6,193,718 B1 | 2/2001 | Kortenbach et al. |
| 5,951,546 | A | 9/1999 | Lorentzen | 6,206,876 B1 | 3/2001 | Levine et al. |
| 5,951,549 | A | 9/1999 | Richardson et al. | 6,206,877 B1 | 3/2001 | Kese et al. |
| 5,954,720 | A | 9/1999 | Wilson et al. | 6,206,893 B1 | 3/2001 | Klein et al. |
| 5,954,731 | A | 9/1999 | Yoon | 6,214,028 B1 | 4/2001 | Yoon et al. |
| 5,954,733 | A | 9/1999 | Yoon | 6,217,602 B1 | 4/2001 | Redmon |
| 5,957,923 | A | 9/1999 | Hahnen et al. | 6,217,615 B1 | 4/2001 | Sioshansi et al. |
| 5,957,937 | A | 9/1999 | Yoon | 6,221,039 B1 | 4/2001 | Durgin et al. |
| 5,960,544 | A | 10/1999 | Beyers | 6,223,100 B1 | 4/2001 | Green |
| 5,961,514 | A | 10/1999 | Long et al. | 6,224,593 B1 | 5/2001 | Ryan et al. |
| 5,964,758 | A | 10/1999 | Dresden | 6,224,614 B1 | 5/2001 | Yoon |
| 5,976,132 | A | 11/1999 | Morris | 6,228,080 B1 | 5/2001 | Gines |
| 5,984,932 | A | 11/1999 | Yoon | 6,228,083 B1 | 5/2001 | Lands et al. |
| 5,984,938 | A | 11/1999 | Yoon | 6,248,124 B1 | 6/2001 | Pedros et al. |

| | | |
|---|---|---|
| 6,248,944 B1 | 6/2001 | Ito |
| 6,261,307 B1 | 7/2001 | Yoon et al. |
| 6,267,761 B1 | 7/2001 | Ryan |
| 6,270,497 B1 | 8/2001 | Sekino et al. |
| 6,270,508 B1 | 8/2001 | Klieman et al. |
| 6,273,887 B1 | 8/2001 | Yamauchi et al. |
| 6,277,117 B1 | 8/2001 | Tetzlaff et al. |
| 6,280,458 B1 | 8/2001 | Boche et al. |
| 6,283,961 B1 | 9/2001 | Underwood et al. |
| D449,886 S | 10/2001 | Tetzlaff et al. |
| 6,298,550 B1 | 10/2001 | Kirwan |
| 6,302,424 B1 | 10/2001 | Gisinger et al. |
| 6,319,262 B1 | 11/2001 | Bates et al. |
| 6,319,451 B1 | 11/2001 | Brune |
| 6,322,561 B1 | 11/2001 | Eggers et al. |
| 6,322,580 B1 | 11/2001 | Kanner |
| 6,325,795 B1 | 12/2001 | Lindemann et al. |
| 6,334,860 B1 | 1/2002 | Dorn |
| 6,334,861 B1 | 1/2002 | Chandler et al. |
| 6,345,532 B1 | 2/2002 | Coudray et al. |
| 6,350,264 B1 | 2/2002 | Hooven |
| 6,352,536 B1 | 3/2002 | Buysse et al. |
| 6,358,249 B1 | 3/2002 | Chen et al. |
| 6,358,259 B1 | 3/2002 | Swain et al. |
| 6,358,268 B1 | 3/2002 | Hunt et al. |
| 6,364,879 B1 | 4/2002 | Chen et al. |
| D457,958 S | 5/2002 | Dycus et al. |
| D457,959 S | 5/2002 | Tetzlaff et al. |
| 6,387,094 B1 | 5/2002 | Eitenmuller |
| 6,391,035 B1 | 5/2002 | Appleby et al. |
| 6,398,779 B1 | 6/2002 | Buysse et al. |
| 6,402,747 B1 | 6/2002 | Lindemann et al. |
| 6,409,728 B1 | 6/2002 | Ehr et al. |
| H2037 H | 7/2002 | Yates et al. |
| 6,419,675 B1 | 7/2002 | Gallo, Sr. |
| 6,425,896 B1 | 7/2002 | Baltschun et al. |
| 6,432,112 B2 | 8/2002 | Brock et al. |
| 6,440,144 B1 | 8/2002 | Bacher |
| 6,443,952 B1 | 9/2002 | Mulier et al. |
| 6,443,970 B1 | 9/2002 | Schulze et al. |
| 6,451,018 B1 | 9/2002 | Lands et al. |
| 6,458,125 B1 | 10/2002 | Cosmescu |
| 6,458,128 B1 | 10/2002 | Schulze |
| 6,458,130 B1 | 10/2002 | Frazier et al. |
| 6,461,352 B2 | 10/2002 | Morgan et al. |
| 6,461,368 B2 | 10/2002 | Fogarty et al. |
| 6,464,701 B1 | 10/2002 | Hooven et al. |
| 6,464,702 B2 | 10/2002 | Schulze et al. |
| 6,464,704 B2 | 10/2002 | Schmaltz et al. |
| 6,485,489 B2 | 11/2002 | Teirstein et al. |
| 6,494,888 B1 | 12/2002 | Laufer |
| 6,500,176 B1 | 12/2002 | Truckai et al. |
| 6,506,196 B1 | 1/2003 | Laufer |
| 6,508,815 B1 | 1/2003 | Strul et al. |
| 6,511,480 B1 | 1/2003 | Tetzlaff et al. |
| 6,514,215 B1 | 2/2003 | Ouchi |
| 6,514,252 B2 | 2/2003 | Nezhat et al. |
| 6,517,539 B1 | 2/2003 | Smith et al. |
| 6,527,771 B1 | 3/2003 | Weadock et al. |
| 6,533,784 B2 | 3/2003 | Truckai et al. |
| 6,545,239 B2 | 4/2003 | Spedale et al. |
| 6,558,385 B1 | 5/2003 | McClurken et al. |
| 6,562,037 B2 | 5/2003 | Paton et al. |
| 6,569,105 B1 | 5/2003 | Kortenbach et al. |
| 6,582,450 B2 | 6/2003 | Ouchi |
| 6,585,735 B1 * | 7/2003 | Frazier et al. ................. 606/51 |
| 6,602,252 B2 | 8/2003 | Mollenauer |
| 6,605,790 B2 | 8/2003 | Yoshida |
| 6,616,658 B2 | 9/2003 | Ineson |
| 6,616,661 B2 | 9/2003 | Wellman et al. |
| 6,620,161 B2 | 9/2003 | Schulze et al. |
| 6,620,184 B2 | 9/2003 | De Laforcade et al. |
| 6,626,901 B1 | 9/2003 | Treat et al. |
| 6,638,287 B2 | 10/2003 | Danitz et al. |
| 6,641,595 B1 | 11/2003 | Moran et al. |
| 6,652,514 B2 | 11/2003 | Ellman et al. |
| 6,652,521 B2 | 11/2003 | Schulze |
| 6,656,175 B2 | 12/2003 | Francischelli et al. |
| 6,656,177 B2 | 12/2003 | Truckai et al. |
| 6,660,072 B2 | 12/2003 | Chatterjee |
| 6,663,639 B1 | 12/2003 | Laufer et al. |
| 6,663,641 B1 | 12/2003 | Kovac et al. |
| 6,666,854 B1 | 12/2003 | Lange |
| 6,669,696 B2 | 12/2003 | Bacher et al. |
| 6,673,092 B1 | 1/2004 | Bacher |
| 6,676,660 B2 | 1/2004 | Wampler et al. |
| 6,676,676 B2 | 1/2004 | Danitz et al. |
| 6,679,882 B1 | 1/2004 | Kornerup |
| 6,682,527 B2 | 1/2004 | Strul |
| 6,682,528 B2 | 1/2004 | Frazier et al. |
| 6,685,724 B1 | 2/2004 | Haluck |
| 6,689,131 B2 | 2/2004 | McClurken |
| 6,692,445 B2 | 2/2004 | Roberts et al. |
| 6,693,246 B1 | 2/2004 | Rudolph et al. |
| 6,695,840 B2 | 2/2004 | Schulze |
| 6,702,810 B2 | 3/2004 | McClurken et al. |
| 6,723,092 B2 | 4/2004 | Brown et al. |
| 6,726,068 B2 | 4/2004 | Miller |
| 6,726,686 B2 | 4/2004 | Buysse et al. |
| 6,726,694 B2 | 4/2004 | Blatter et al. |
| 6,733,498 B2 | 5/2004 | Paton et al. |
| 6,736,813 B2 | 5/2004 | Yamauchi et al. |
| 6,743,229 B2 | 6/2004 | Buysse et al. |
| 6,743,230 B2 | 6/2004 | Lutze et al. |
| 6,743,239 B1 | 6/2004 | Kuehn et al. |
| 6,743,240 B2 | 6/2004 | Smith et al. |
| 6,755,843 B2 | 6/2004 | Chung et al. |
| 6,756,553 B1 | 6/2004 | Yamaguchi et al. |
| 6,757,977 B2 | 7/2004 | Dambal et al. |
| D493,888 S | 8/2004 | Reschke |
| 6,770,072 B1 | 8/2004 | Truckai |
| 6,773,409 B2 | 8/2004 | Truckai et al. |
| 6,773,432 B1 | 8/2004 | Clayman et al. |
| 6,773,434 B2 | 8/2004 | Ciarrocca |
| 6,773,441 B1 | 8/2004 | Laufer et al. |
| 6,775,575 B2 | 8/2004 | Bommannan et al. |
| 6,776,780 B2 | 8/2004 | Mulier et al. |
| 6,786,905 B2 | 9/2004 | Swanson et al. |
| 6,790,217 B2 | 9/2004 | Schulze et al. |
| 6,796,981 B2 | 9/2004 | Wham et al. |
| D496,997 S | 10/2004 | Dycus et al. |
| 6,800,825 B1 | 10/2004 | Sasaki et al. |
| 6,802,843 B2 | 10/2004 | Truckai et al. |
| 6,808,525 B2 | 10/2004 | Latterell et al. |
| D499,181 S | 11/2004 | Dycus et al. |
| 6,818,000 B2 | 11/2004 | Muller et al. |
| 6,821,285 B2 | 11/2004 | Laufer et al. |
| 6,835,200 B2 | 12/2004 | Laufer et al. |
| 6,857,357 B2 | 2/2005 | Fujii |
| 6,860,880 B2 | 3/2005 | Treat et al. |
| 6,887,240 B1 | 5/2005 | Lands et al. |
| 6,889,116 B2 | 5/2005 | Jinno |
| 6,914,201 B2 | 7/2005 | Van Vooren et al. |
| 6,926,716 B2 | 8/2005 | Baker et al. |
| 6,929,644 B2 | 8/2005 | Truckai et al. |
| 6,932,810 B2 | 8/2005 | Ryan |
| 6,932,816 B2 | 8/2005 | Phan |
| 6,934,134 B2 | 8/2005 | Mori et al. |
| 6,936,061 B2 | 8/2005 | Sasaki |
| D509,297 S | 9/2005 | Wells |
| 6,942,662 B2 | 9/2005 | Goble et al. |
| 6,943,311 B2 | 9/2005 | Miyako |
| 6,953,430 B2 | 10/2005 | Kodooka |
| 6,953,461 B2 | 10/2005 | McClurken et al. |
| 6,958,070 B2 | 10/2005 | Witt et al. |
| 6,960,210 B2 | 11/2005 | Lands et al. |

| Patent No. | Date | Name |
|---|---|---|
| 6,964,662 B2 | 11/2005 | Kidooka |
| 6,966,907 B2 | 11/2005 | Goble |
| 6,972,017 B2 | 12/2005 | Smith et al. |
| 6,977,495 B2 | 12/2005 | Donofrio |
| 6,979,786 B2 | 12/2005 | Aukland et al. |
| 6,981,628 B2 | 1/2006 | Wales |
| 6,987,244 B2 | 1/2006 | Bauer |
| 6,994,707 B2 | 2/2006 | Ellman et al. |
| 6,994,709 B2 | 2/2006 | Iida |
| 6,997,931 B2 | 2/2006 | Sauer et al. |
| 7,001,381 B2 | 2/2006 | Harano et al. |
| 7,011,657 B2 | 3/2006 | Truckai et al. |
| 7,033,354 B2 | 4/2006 | Keppel |
| 7,033,356 B2 | 4/2006 | Latterell et al. |
| 7,041,102 B2 | 5/2006 | Truckai et al. |
| 7,044,948 B2 | 5/2006 | Keppel |
| 7,052,489 B2 | 5/2006 | Griego et al. |
| 7,052,496 B2 | 5/2006 | Yamauchi |
| 7,063,715 B2 | 6/2006 | Onuki et al. |
| D525,361 S | 7/2006 | Hushka |
| 7,070,597 B2 | 7/2006 | Truckai et al. |
| 7,083,618 B2 | 8/2006 | Couture et al. |
| 7,083,619 B2 | 8/2006 | Truckai et al. |
| 7,083,620 B2 | 8/2006 | Jahns et al. |
| 7,087,051 B2 | 8/2006 | Bourne et al. |
| 7,087,054 B2 | 8/2006 | Truckai et al. |
| 7,090,673 B2 | 8/2006 | Dycus et al. |
| 7,090,689 B2 | 8/2006 | Nagase et al. |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,103,947 B2 | 9/2006 | Sartor et al. |
| 7,107,124 B2 | 9/2006 | Green |
| 7,112,199 B2 | 9/2006 | Cosmescu |
| D531,311 S | 10/2006 | Guerra et al. |
| 7,115,123 B2 | 10/2006 | Knowlton et al. |
| 7,118,570 B2 | 10/2006 | Tetzlaff et al. |
| 7,118,587 B2 | 10/2006 | Dycus et al. |
| 7,131,860 B2 | 11/2006 | Sartor et al. |
| 7,131,970 B2 | 11/2006 | Moses et al. |
| 7,131,971 B2 | 11/2006 | Dycus et al. |
| 7,135,020 B2 | 11/2006 | Lawes et al. |
| D533,942 S | 12/2006 | Kerr et al. |
| 7,145,757 B2 | 12/2006 | Shea et al. |
| 7,147,638 B2 | 12/2006 | Chapman et al. |
| 7,150,097 B2 | 12/2006 | Sremcich et al. |
| 7,150,749 B2 | 12/2006 | Dycus et al. |
| 7,153,314 B2 | 12/2006 | Laufer et al. |
| D535,027 S | 1/2007 | James et al. |
| 7,156,842 B2 | 1/2007 | Sartor et al. |
| 7,156,846 B2 | 1/2007 | Dycus et al. |
| 7,160,298 B2 | 1/2007 | Lawes et al. |
| 7,160,299 B2 | 1/2007 | Baily |
| 7,169,146 B2 | 1/2007 | Truckai et al. |
| 7,179,255 B2 | 2/2007 | Lettice et al. |
| 7,179,258 B2 | 2/2007 | Buysse et al. |
| 7,195,631 B2 | 3/2007 | Dumbauld |
| D541,418 S | 4/2007 | Schechter et al. |
| 7,207,990 B2 | 4/2007 | Lands et al. |
| D541,938 S | 5/2007 | Kerr et al |
| 7,223,264 B2 | 5/2007 | Daniel et al. |
| 7,223,265 B2 | 5/2007 | Keppel |
| 7,232,440 B2 | 6/2007 | Dumbauld et al. |
| 7,241,288 B2 | 7/2007 | Braun |
| 7,241,296 B2 | 7/2007 | Buysse et al. |
| 7,244,257 B2 | 7/2007 | Podjahsky et al. |
| 7,246,734 B2 | 7/2007 | Shelto, IV |
| 7,248,944 B2 | 7/2007 | Green |
| 7,252,667 B2 | 8/2007 | Moses et al. |
| 7,255,697 B2 | 8/2007 | Dycus et al. |
| 7,267,677 B2 | 9/2007 | Johnson et al. |
| 7,270,660 B2 | 9/2007 | Ryan |
| 7,270,664 B2 | 9/2007 | Johnson et al. |
| 7,276,068 B2 | 10/2007 | Johnson et al. |
| 7,300,435 B2 | 11/2007 | Wham et al. |
| 7,303,557 B2 | 12/2007 | Wham et al. |
| 7,311,709 B2 | 12/2007 | Truckai et al. |
| 7,314,471 B2 | 1/2008 | Holman |
| 7,318,823 B2 | 1/2008 | Sharps et al. |
| 7,329,256 B2 | 2/2008 | Johnson et al. |
| 7,329,257 B2 | 2/2008 | Kanehira et al. |
| D564,662 S | 3/2008 | Moses et al. |
| 7,338,526 B2 | 3/2008 | Steinberg |
| 7,342,754 B2 | 3/2008 | Fitzgerald et al. |
| 7,344,268 B2 | 3/2008 | Jigamian |
| D567,943 S | 4/2008 | Moses et al. |
| 7,367,976 B2 | 5/2008 | Lawes et al. |
| 7,377,920 B2 | 5/2008 | Buysse et al. |
| 7,384,420 B2 | 6/2008 | Dycus et al. |
| 7,384,421 B2 | 6/2008 | Hushka |
| 7,396,336 B2 | 7/2008 | Orszulak et al. |
| D575,395 S | 8/2008 | Hushka |
| D575,401 S | 8/2008 | Hixson et al. |
| 7,435,249 B2 | 10/2008 | Buysse et al. |
| 7,442,193 B2 | 10/2008 | Shields et al. |
| 7,442,194 B2 | 10/2008 | Dumbauld et al. |
| 7,445,621 B2 | 11/2008 | Dumbauld et al. |
| 7,458,972 B2 | 12/2008 | Keppel |
| 7,473,253 B2 | 1/2009 | Dycus et al. |
| 7,481,810 B2 | 1/2009 | Dumbauld et al. |
| 7,487,780 B2 | 2/2009 | Hooven |
| 7,491,201 B2 * | 2/2009 | Shields et al. ............... 606/51 |
| 7,491,202 B2 * | 2/2009 | Odom et al. ............... 606/51 |
| 7,500,975 B2 | 3/2009 | Cunningham et al. |
| 7,510,556 B2 | 3/2009 | Nguyen et al. |
| 7,513,898 B2 | 4/2009 | Johnson et al. |
| 7,540,872 B2 | 6/2009 | Schechter et al. |
| 7,549,995 B2 | 6/2009 | Schultz |
| 7,553,312 B2 | 6/2009 | Tetzlaff et al. |
| 2002/0013583 A1 | 1/2002 | Camran et al. |
| 2002/0049442 A1 | 4/2002 | Roberts et al. |
| 2002/0099372 A1 | 7/2002 | Schulze et al. |
| 2002/0107517 A1 | 8/2002 | Witt et al. |
| 2002/0111624 A1 | 8/2002 | Witt et al. |
| 2002/0188294 A1 | 12/2002 | Couture et al. |
| 2003/0014052 A1 | 1/2003 | Buysse et al. |
| 2003/0014053 A1 | 1/2003 | Nguyen et al. |
| 2003/0018331 A1 | 1/2003 | Dycus et al. |
| 2003/0018332 A1 | 1/2003 | Schmaltz et al. |
| 2003/0032956 A1 | 2/2003 | Lands et al. |
| 2003/0069570 A1 | 4/2003 | Witzel et al. |
| 2003/0069571 A1 * | 4/2003 | Treat et al. ............... 606/29 |
| 2003/0078578 A1 | 4/2003 | Truckai et al. |
| 2003/0109875 A1 | 6/2003 | Tetzlaff et al. |
| 2003/0114851 A1 | 6/2003 | Truckai et al. |
| 2003/0139741 A1 | 7/2003 | Goble et al. |
| 2003/0139742 A1 | 7/2003 | Wampler et al. |
| 2003/0158548 A1 | 8/2003 | Phan et al. |
| 2003/0158549 A1 | 8/2003 | Swanson |
| 2003/0171747 A1 | 9/2003 | Kanehira et al. |
| 2003/0181910 A1 | 9/2003 | Dycus et al. |
| 2003/0199869 A1 | 10/2003 | Johnson et al. |
| 2003/0216732 A1 | 11/2003 | Truckai et al. |
| 2003/0220637 A1 | 11/2003 | Truckai et al. |
| 2003/0229344 A1 | 12/2003 | Dycus et al. |
| 2003/0236325 A1 | 12/2003 | Bonora |
| 2003/0236518 A1 | 12/2003 | Marchitto et al. |
| 2004/0030330 A1 | 2/2004 | Brassell et al. |
| 2004/0030332 A1 | 2/2004 | Knowlton et al. |
| 2004/0049185 A1 | 3/2004 | Latterell et al. |
| 2004/0064151 A1 | 4/2004 | Mollenauer |
| 2004/0073238 A1 | 4/2004 | Makower |
| 2004/0073256 A1 | 4/2004 | Marchitto et al. |
| 2004/0078035 A1 | 4/2004 | Kanehira et al. |
| 2004/0082952 A1 | 4/2004 | Dycus et al. |
| 2004/0087943 A1 | 5/2004 | Dycus et al. |

| | | | | | | |
|---|---|---|---|---|---|---|
| 2004/0115296 A1 | 6/2004 | Duffin | | 2006/0253126 A1 | 11/2006 | Bjerken et al. |
| 2004/0116924 A1 | 6/2004 | Dycus et al. | | 2006/0259036 A1 | 11/2006 | Tetzlaf et al. |
| 2004/0116979 A1 | 6/2004 | Truckai et al. | | 2006/0264922 A1 | 11/2006 | Sartor et al. |
| 2004/0122423 A1 | 6/2004 | Dycus et al. | | 2006/0264931 A1 | 11/2006 | Chapman et al. |
| 2004/0143263 A1 | 7/2004 | Schechter et al. | | 2006/0271038 A1 | 11/2006 | Johnson et al. |
| 2004/0147925 A1 | 7/2004 | Buysse et al. | | 2006/0283093 A1 | 12/2006 | Petrovic et al. |
| 2004/0148035 A1 | 7/2004 | Barrett et al. | | 2006/0287641 A1 | 12/2006 | Perlin |
| 2004/0162557 A1 | 8/2004 | Tetzlaff et al. | | 2007/0016182 A1 | 1/2007 | Lipson et al. |
| 2004/0176762 A1 | 9/2004 | Lawes et al. | | 2007/0016187 A1 | 1/2007 | Weinberg et al. |
| 2004/0193153 A1 | 9/2004 | Sartor et al. | | 2007/0043352 A1 | 2/2007 | Garrison et al. |
| 2004/0199181 A1 | 10/2004 | Knodel et al. | | 2007/0043353 A1 | 2/2007 | Dycus et al. |
| 2004/0210282 A1 | 10/2004 | Flock et al. | | 2007/0055231 A1 | 3/2007 | Dycus et al. |
| 2004/0224590 A1 | 11/2004 | Rawa et al. | | 2007/0060919 A1 | 3/2007 | Isaacson et al. |
| 2004/0225288 A1 | 11/2004 | Buysse et al. | | 2007/0062017 A1 | 3/2007 | Dycus et al. |
| 2004/0230189 A1 | 11/2004 | Keppel | | 2007/0074807 A1 | 4/2007 | Guerra |
| 2004/0236326 A1 | 11/2004 | Schulze et al. | | 2007/0078456 A1 | 4/2007 | Dumbauld et al. |
| 2004/0243125 A1 | 12/2004 | Dycus et al. | | 2007/0078458 A1 | 4/2007 | Dumbauld et al. |
| 2004/0249371 A1 | 12/2004 | Dycus et al. | | 2007/0078459 A1 | 4/2007 | Johnson et al. |
| 2004/0249374 A1 | 12/2004 | Tetzlaff et al. | | 2007/0088356 A1 | 4/2007 | Moses et al. |
| 2004/0250419 A1 | 12/2004 | Sremcich et al. | | 2007/0106295 A1 | 5/2007 | Garrison et al. |
| 2004/0254573 A1 | 12/2004 | Dycus et al. | | 2007/0106297 A1 | 5/2007 | Dumbauld et al. |
| 2004/0260281 A1 | 12/2004 | Baxter, III et al. | | 2007/0118111 A1 | 5/2007 | Weinberg |
| 2005/0004564 A1 | 1/2005 | Wham et al. | | 2007/0118115 A1 | 5/2007 | Artale et al. |
| 2005/0004568 A1 | 1/2005 | Lawes et al. | | 2007/0142833 A1 | 6/2007 | Dycus et al. |
| 2005/0004569 A1 | 1/2005 | Witt et al. | | 2007/0142834 A1 | 6/2007 | Dumbauld |
| 2005/0004570 A1 | 1/2005 | Chapman et al. | | 2007/0156139 A1 | 7/2007 | Schechter et al. |
| 2005/0021025 A1 | 1/2005 | Buysse et al. | | 2007/0156140 A1 | 7/2007 | Baily |
| 2005/0021026 A1 | 1/2005 | Baily | | 2007/0173811 A1 | 7/2007 | Couture et al. |
| 2005/0021027 A1 * | 1/2005 | Shields et al. ............ 606/51 | | 2007/0173814 A1 | 7/2007 | Hixson et al. |
| 2005/0033278 A1 | 2/2005 | McClurken et al. | | 2007/0179499 A1 | 8/2007 | Garrison |
| 2005/0059934 A1 | 3/2005 | Wenchell et al. | | 2007/0198011 A1 | 8/2007 | Sugita |
| 2005/0096645 A1 | 5/2005 | Wellman et al. | | 2007/0203485 A1 | 8/2007 | Keppel |
| 2005/0101949 A1 * | 5/2005 | Harano et al. ............ 606/40 | | 2007/0213706 A1 | 9/2007 | Dumbauld et al. |
| 2005/0101951 A1 | 5/2005 | Wham et al. | | 2007/0213707 A1 | 9/2007 | Dumbauld et al. |
| 2005/0101952 A1 | 5/2005 | Lands et al. | | 2007/0213708 A1 | 9/2007 | Dumbauld et al. |
| 2005/0107784 A1 | 5/2005 | Moses et al. | | 2007/0213712 A1 | 9/2007 | Buysse et al. |
| 2005/0107785 A1 | 5/2005 | Dycus et al. | | 2007/0255279 A1 | 11/2007 | Buysse et al. |
| 2005/0113818 A1 | 5/2005 | Sartor et al. | | 2007/0260235 A1 | 11/2007 | Podhajsky |
| 2005/0113819 A1 | 5/2005 | Wham et al. | | 2007/0260238 A1 | 11/2007 | Guerra |
| 2005/0113826 A1 | 5/2005 | Johnson et al. | | 2007/0260241 A1 | 11/2007 | Dalla Betta et al. |
| 2005/0113827 A1 | 5/2005 | Dumbauld et al. | | 2007/0260242 A1 | 11/2007 | Dycus et al. |
| 2005/0113828 A1 | 5/2005 | Shields et al. | | 2007/0265616 A1 | 11/2007 | Couture et al. |
| 2005/0119655 A1 | 6/2005 | Moses et al. | | 2008/0004616 A1 | 1/2008 | Patrick |
| 2005/0149017 A1 | 7/2005 | Dycus | | 2008/0009860 A1 | 1/2008 | Odom |
| 2005/0149151 A1 | 7/2005 | Orszulak et al. | | 2008/0015575 A1 | 1/2008 | Odom et al. |
| 2005/0154387 A1 | 7/2005 | Moses et al. | | 2008/0021450 A1 | 1/2008 | Couture |
| 2005/0187547 A1 | 8/2005 | Sugi | | 2008/0033428 A1 | 2/2008 | Artale et al. |
| 2005/0197659 A1 | 9/2005 | Bahney | | 2008/0039835 A1 | 2/2008 | Johnson et al. |
| 2005/0203504 A1 | 9/2005 | Wham et al. | | 2008/0039836 A1 * | 2/2008 | Odom et al. ............ 606/51 |
| 2005/0240179 A1 | 10/2005 | Buysse et al. | | 2008/0045947 A1 | 2/2008 | Johnson et al. |
| 2006/0052778 A1 | 3/2006 | Chapman et al. | | 2008/0058802 A1 | 3/2008 | Couture et al. |
| 2006/0052779 A1 | 3/2006 | Hammill | | 2008/0082100 A1 | 4/2008 | Orton et al. |
| 2006/0064085 A1 | 3/2006 | Schechter et al. | | 2008/0091189 A1 | 4/2008 | Carlton |
| 2006/0064086 A1 | 3/2006 | Odom | | 2008/0114356 A1 | 5/2008 | Johnson et al. |
| 2006/0074417 A1 | 4/2006 | Cunningham et al. | | 2008/0167651 A1 | 7/2008 | Tetzlaff et al. |
| 2006/0079888 A1 | 4/2006 | Mulier et al. | | 2008/0195093 A1 | 8/2008 | Couture et al. |
| 2006/0079890 A1 | 4/2006 | Guerra | | 2008/0215051 A1 | 9/2008 | Buysse et al. |
| 2006/0079891 A1 | 4/2006 | Arts et al. | | 2008/0243120 A1 | 10/2008 | Lawes et al. |
| 2006/0079933 A1 | 4/2006 | Hushka et al. | | 2008/0249527 A1 | 10/2008 | Couture |
| 2006/0084973 A1 | 4/2006 | Hushka | | 2008/0312653 A1 | 12/2008 | Arts et al. |
| 2006/0089670 A1 | 4/2006 | Hushka | | 2008/0319442 A1 | 12/2008 | Unger et al. |
| 2006/0116675 A1 | 6/2006 | McClurken et al. | | 2009/0012520 A1 | 1/2009 | Hixson et al. |
| 2006/0129146 A1 | 6/2006 | Dycus et al. | | 2009/0018535 A1 | 1/2009 | Schechter et al. |
| 2006/0161150 A1 | 7/2006 | Keppel | | 2009/0024126 A1 | 1/2009 | Artale et al. |
| 2006/0167450 A1 | 7/2006 | Johnson et al. | | 2009/0043304 A1 | 2/2009 | Tetzlaff et al. |
| 2006/0167452 A1 | 7/2006 | Moses et al. | | 2009/0048596 A1 | 2/2009 | Shields et al. |
| 2006/0173452 A1 | 8/2006 | Buysse et al. | | 2009/0062794 A1 | 3/2009 | Buysse et al. |
| 2006/0189980 A1 | 8/2006 | Johnson et al. | | 2009/0082766 A1 | 3/2009 | Unger et al. |
| 2006/0189981 A1 | 8/2006 | Dycus et al. | | 2009/0082767 A1 | 3/2009 | Unger et al. |
| 2006/0190035 A1 | 8/2006 | Hushka et al. | | 2009/0082769 A1 | 3/2009 | Unger et al. |
| 2006/0217709 A1 | 9/2006 | Couture et al. | | 2009/0088738 A1 | 4/2009 | Guerra et al. |
| 2006/0224158 A1 | 10/2006 | Odom et al. | | 2009/0088739 A1 | 4/2009 | Hushka et al. |
| 2006/0229666 A1 | 10/2006 | Suzuki et al. | | 2009/0088740 A1 | 4/2009 | Guerra et al. |

| | | | | | | |
|---|---|---|---|---|---|---|
| 2009/0088741 A1 | 4/2009 | Hushka et al. | EP | 1532932 A1 | 5/2005 | |
| 2009/0088744 A1 | 4/2009 | Townsend | EP | 1535581 A2 | 6/2005 | |
| 2009/0088745 A1 | 4/2009 | Hushka et al. | EP | 1609430 A1 | 12/2005 | |
| 2009/0088746 A1 | 4/2009 | Hushka et al. | EP | 1632192 A1 | 3/2006 | |
| 2009/0088747 A1 | 4/2009 | Hushka et al. | EP | 1642543 | 4/2006 | |
| 2009/0088748 A1 | 4/2009 | Guerra et al. | EP | 1645238 A1 | 4/2006 | |
| 2009/0088749 A1 | 4/2009 | Hushka et al. | EP | 1645240 A2 | 4/2006 | |
| 2009/0088750 A1 | 4/2009 | Hushka et al. | EP | 1649821 | 4/2006 | |
| 2009/0112206 A1 | 4/2009 | Dumbauld et al. | EP | 1707143 A1 | 10/2006 | |
| 2009/0131934 A1 | 5/2009 | Odom et al. | EP | 1769765 | 4/2007 | |
| 2009/0149853 A1 | 6/2009 | Shields et al. | EP | 1769766 | 4/2007 | |
| 2009/0149854 A1 | 6/2009 | Cunningham et al. | EP | 1929970 | 6/2008 | |
| 2009/0171350 A1 | 7/2009 | Dycus et al. | EP | 1683496 | 12/2008 | |
| 2009/0171353 A1 | 7/2009 | Johnson et al. | GB | 623316 | 5/1949 | |
| 2009/0182327 A1 | 7/2009 | Unger | GB | 1490585 | 11/1977 | |
| 2009/0187188 A1 | 7/2009 | Guerra et al. | GB | 2214430 A | 6/1989 | |

FOREIGN PATENT DOCUMENTS

| | | | | | |
|---|---|---|---|---|---|
| GB | 2213416 | 8/1989 | | | |
| JP | 501068 | 9/1984 | | | |
| DE | 2415263 | 10/1975 | JP | 502328 | 3/1992 |
| DE | 2514501 | 10/1976 | JP | 5-5106 | 1/1993 |
| DE | 2627679 | 1/1977 | JP | 5-40112 | 2/1993 |
| DE | 3612646 | 4/1987 | JP | 06343644 A2 | 12/1994 |
| DE | 8712328 | 3/1988 | JP | 07265328 A2 | 10/1995 |
| DE | 4303882 | 8/1994 | JP | 08056955 A2 | 3/1996 |
| DE | 4403252 | 8/1995 | JP | 08252263 A2 | 10/1996 |
| DE | 19515914 | 7/1996 | JP | 09010223 A2 | 1/1997 |
| DE | 29616210 | 1/1997 | JP | 11244298 A2 | 9/1999 |
| DE | 19608716 | 4/1997 | JP | 2000342599 A2 | 12/2000 |
| DE | 19751106 | 5/1998 | JP | 2000350732 A2 | 12/2000 |
| DE | 19751108 | 5/1999 | JP | 2001008944 A2 | 1/2001 |
| DE | 19738457 | 1/2009 | JP | 2001029356 A2 | 2/2001 |
| EP | 0364216 A1 | 4/1990 | JP | 2001128990 A2 | 5/2001 |
| EP | 0467501 | 1/1992 | RU | 401367 | 11/1974 |
| EP | 518230 A1 | 12/1992 | WO | WO89/00757 | 1/1989 |
| EP | 541 930 B1 | 5/1993 | WO | WO 92/04873 | 4/1992 |
| EP | 0572131 | 12/1993 | WO | WO 92/06642 | 4/1992 |
| EP | 584787 A1 | 3/1994 | WO | WO 93/21845 | 11/1993 |
| EP | 0589453 A2 | 3/1994 | WO | WO 94/08524 A | 4/1994 |
| EP | 0589555 | 3/1994 | WO | WO94/20025 | 9/1994 |
| EP | 0623316 A1 | 11/1994 | WO | WO 95/02369 | 1/1995 |
| EP | 0624348 A2 | 11/1994 | WO | WO 95/07662 | 3/1995 |
| EP | 0650701 A1 | 5/1995 | WO | WO95/07662 | 3/1995 |
| EP | 0694290 A3 | 3/1996 | WO | WO95/15124 | 6/1995 |
| EP | 0717966 A1 | 6/1996 | WO | WO96/05776 | 2/1996 |
| EP | 0754437 A3 | 3/1997 | WO | WO 96/22056 | 7/1996 |
| EP | 0517243 | 9/1997 | WO | WO 96/13218 | 9/1996 |
| EP | 853922 A1 | 7/1998 | WO | WO 97/00646 | 1/1997 |
| EP | 0875209 A1 | 11/1998 | WO | WO 97/00647 | 1/1997 |
| EP | 0878169 A1 | 11/1998 | WO | WO97/10764 | 3/1997 |
| EP | 0887046 A3 | 1/1999 | WO | WO 97/10764 | 3/1997 |
| EP | 0923907 A1 | 6/1999 | WO | WO 97/24073 | 7/1997 |
| EP | 0986990 A1 | 3/2000 | WO | WO 97/24993 | 7/1997 |
| EP | 1034747 A1 | 9/2000 | WO | WO 98/27880 | 7/1998 |
| EP | 1034748 A1 | 9/2000 | WO | WO 99/03407 | 1/1999 |
| EP | 1025807 A3 | 10/2000 | WO | WO 99/03408 | 1/1999 |
| EP | 1034746 A3 | 10/2000 | WO | WO 99/03409 | 1/1999 |
| EP | 1050278 A1 | 11/2000 | WO | WO 99/12488 | 3/1999 |
| EP | 1053719 A1 | 11/2000 | WO | WO 99/23933 | 5/1999 |
| EP | 1053720 A1 | 11/2000 | WO | WO 99/40857 | 8/1999 |
| EP | 1055399 A1 | 11/2000 | WO | WO 99/40861 | 8/1999 |
| EP | 1055400 A1 | 11/2000 | WO | WO 99/51158 | 10/1999 |
| EP | 1080694 A1 | 3/2001 | WO | WO 99/66850 A | 12/1999 |
| EP | 1082944 A1 | 3/2001 | WO | WO 00/24330 | 5/2000 |
| EP | 1159926 A2 | 12/2001 | WO | WO 00/24331 | 5/2000 |
| EP | 1177771 | 2/2002 | WO | WO00/24331 | 5/2000 |
| EP | 1301135 A | 4/2003 | WO | WO 00/36986 | 6/2000 |
| EP | 1330991 A1 | 7/2003 | WO | WO 00/41638 | 7/2000 |
| EP | 1486177 A2 | 6/2004 | WO | WO00/47124 | 8/2000 |
| EP | 1472984 A1 | 11/2004 | WO | WO 00/53112 | 9/2000 |
| EP | 0774232 | 1/2005 | WO | WO 01/17448 A | 3/2001 |
| EP | 1527747 A2 | 5/2005 | WO | WO 01/54604 | 8/2001 |
| EP | 1530952 A1 | 5/2005 | WO | WO02/07627 | 1/2002 |
| | | | WO | WO 02/07627 | 1/2002 |

| | | |
|---|---|---|
| WO | WO 02/067798 A1 | 9/2002 |
| WO | WO 02/080783 | 10/2002 |
| WO | WO02/080783 | 10/2002 |
| WO | WO 02/080784 | 10/2002 |
| WO | WO02/080784 | 10/2002 |
| WO | WO02/080785 | 10/2002 |
| WO | WO 02/080785 | 10/2002 |
| WO | WO 02/080786 | 10/2002 |
| WO | WO02/080786 | 10/2002 |
| WO | WO02/080793 | 10/2002 |
| WO | WO 02/080793 | 10/2002 |
| WO | WO 02/080794 | 10/2002 |
| WO | WO02/080794 | 10/2002 |
| WO | WO 02/080795 | 10/2002 |
| WO | WO 02/080796 | 10/2002 |
| WO | WO02/080797 | 10/2002 |
| WO | WO 02/080797 | 10/2002 |
| WO | WO 02/080798 | 10/2002 |
| WO | WO 02/080799 | 10/2002 |
| WO | WO 02/081170 | 10/2002 |
| WO | WO02/081170 | 10/2002 |
| WO | WO 03/061500 | 7/2003 |
| WO | WO 03/090630 A3 | 11/2003 |
| WO | WO 03/101311 | 12/2003 |
| WO | WO 2004/032776 A1 | 4/2004 |
| WO | WO2004/032777 | 4/2004 |
| WO | WO 2004/032777 | 4/2004 |
| WO | WO 2004/052221 | 6/2004 |
| WO | WO 2004/073488 A2 | 9/2004 |
| WO | WO 2004/073490 | 9/2004 |
| WO | WO2004/073490 | 9/2004 |
| WO | WO2004/073753 | 9/2004 |
| WO | WO 2004/082495 | 9/2004 |
| WO | WO 2004/098383 | 11/2004 |
| WO | WO 2004/103156 | 12/2004 |
| WO | WO 2005/004734 A1 | 1/2005 |
| WO | WO2005/004735 | 1/2005 |
| WO | WO 2005/110264 | 11/2005 |
| WO | WO 2008/045348 | 4/2008 |
| WO | WO 2008/045350 | 4/2008 |

OTHER PUBLICATIONS

Int'l Search Report EP 06005185.1 dated Apr. 18, 2006.
Int'l Search Report EP 06008779.8 dated Jun. 13, 2006.
Int'l Search Report EP 1683496 dated Jun. 13, 2006.
Int'l Search Report EP 04013772 dated Apr. 1, 2005.
Int'l Search Report EP 05013895 dated Oct. 14, 2005.
Int'l Search Report EP 05017281 dated Nov. 16, 2005.
Int'l Search Report EP 06006716 dated Aug. 4, 2006.
Int'l Search Report PCT/US01/11224 dated Nov. 13, 2001.
Int'l Search Report EP 06014461.5 dated Oct. 20, 2006.
Int'l Search Report EP 06020584.6 dated Jan. 12, 2007.
Int'l Search Report EP 06020583.8 dated Jan. 30, 2007.
Int'l Search Report EP 06020756.0 dated Feb. 5, 2007.
Int'l Search Report EP 06024123.9 dated Feb. 26, 2007.
Int'l Search Report EP 06 020574.7 dated Sep. 21, 2007.
Int'l Search Report EP 07 010672.9 dated Oct. 1, 2007.
Int'l Search Report EP 07 013779.9 dated Oct. 18, 2007.
Int'l Search Report EP 07 009026.1 dated Sep. 12, 2007.
Int'l Search Report EP 07 015601.3 dated Dec. 6, 2007.
Int'l Search Report EP 07 015191.5 dated Dec. 19, 2007.
Int'l Search Report EP 07 020283.3 dated Jan. 16, 2008.
Sigel et al. "The Mechanism of Blood Vessel Closure by High Frequency Electrocoagulation" Surgery Gynecology & Obstetrics, Oct. 1965 pp. 823-831.
Bergdahl et al. "Studies on Coagulation and the Development of an Automatic Computerized Bipolar Coagulator" J. Neurosurg, vol. 75, Jul. 1991, pp. 148-151.
Kennedy et al. "High-burst-strength, feedback-controlled bipolar vessel sealing" Surgical Endoscopy (1998) 12: 876-878.

Peterson et al. "Comparison of Healing Process Following Ligation with Sutures and Bipolar Vessel Sealing" Surgical Technology International (2001).
Linehan et al. "A Phase I Study of the LigaSure Vessel Sealing System in Hepatic Surgery" Section of HP8 Surger, Washington University School of Medicine, St. Louis MO, Presented at AHPBA, Feb. 2001.
Johnson et al. "Evaluation of the LigaSure Vessel Sealing System in Hemorrhoidectormy" American College of Surgeons (ACS) Clinicla Congress Poster (2000).
Sayfan et al. "Sutureless Closed Hemorrhoidectomy: A New Technique" Annals of Surgery vol. 234 No. 1 Jul. 2001 pp. 21-24.
Heniford et al. "Initial Results with an Electrothermal Bipolar Vessel Sealer" Surgical Endoscopy (2000) 15:799-801.
Heniford et al. "Initial Research and Clinical Results with an Electrothermal Bipolar Vessel Sealer" Oct. 1999.
McLellan et al. "Vessel Sealing for Hemostasis During Pelvic Surgery" Int'l Federation of Gynecology and Obstetrics FIGO World Congress 2000, Washington, D.C.
Levy et al. " Use of a New Energy-based Vessel Ligation Device During Vaginal Hysterectomy" Int'l Federation of Gynecology and Obstetrics (FIGO) World Congress 1999.
Crawford et al. "Use of the LigaSure Vessel Sealing System in Urologic Cancer Surger" Grand Rounds in Urology 1999 vol. 1 Issue 4 pp. 10-17.
Rothenberg et al. "Use of the LigaSure Vessel Sealing System in Minimally Invasive Surgery in Children" Int'l Pediatric Endosurgery Group (IPEG) 2000.
Palazzo et al. "Randomized clinical trial of Ligasure versus open haemorrhoidectomy" British Journal of Surgery 2002, 89, 154-157.
"Innovations in Electrosurgery" Sales/Product Literature; Dec. 31, 2000.
LigaSure Vessel Sealing System, the Seal of Confidence in General, Gynecologic, Urologic, and Laparaoscopic Surgery Sales/Product Literature; Jan. 2004.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC 2003.
"Reducing Needlestick Injuries in the Operating Room" Sales/Product Literature 2001.
Chung et al., "Clinical Experience of Sutureless Closed Hemorrhoidectomy with LigaSure" Diseases of the Colon & Rectum vol. 46, No. 1 Jan. 2003.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Paul G. Horgan, "A Novel Technique for Parenchymal Division During Hepatectomy" The American Journal of Surgery, vol. 181, No. 3, Apr. 2001 pp. 236-237.
W. Scott Helton, "LigaSure Vessel Sealing System: Revolutionary Hemostasis Product for General Surgery" Sales/Product Literature 1999.
Michael Choti, "Abdominoperineal Resection with the LigaSure Vessel Sealing System and LigaSure Atlas 20 cm Open Instrument" Innovations That Work, Jun. 2003.
Craig Johnson, "Use of the LigaSure Vessel Sealing System in Bloodless Hemorrhoidectomy" Innovations That Work, Mar. 2000.
Muller et al., "Extended Left Hemicolectomy Using the LigaSure Vessel Sealing System" Innovations That Work, Sep. 1999.
Herman et al., "Laparoscopic Intestinal Resection With the LigaSure Vessel Sealing System: A Case Report" Innovations That Work, Feb. 2002.
Carus et al., "Initial Experience With The LigaSure Vessel Sealing System in Abdominal Surgery" Innovations That Work, Jun. 2002.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
Levy et al., "Update on Hysterectomy—New Technologies and Techniques" OBG Management, Feb. 2003.
Barbara Levy, "Use of a New Vessel Ligation Device During Vaginal Hysterectomy" FIGO 2000, Washington, D.C.

McLellan et al. "Vessel Sealing For Hemostasis During Gynecologic Surgery" Sales/Product Literature 1999.
Sengupta et al., "Use of a Computer-Controlled Bipolar Diathermy System in Radical Prostatectomies and Other Open Urological Surgery" ANZ Journal of Surgery (2001) 71.9 pp. 538-540.
Olsson et al. "Radical Cystectomy in Females" Current Surgical Techniques in Urology, vol. 14, Issue 3, 2001.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
E. David Crawford "Evaluation of a New Vessel Sealing Device in Urologic Cancer Surgery" Sales/Product Literature 2000.
Joseph Ortenberg "LigaSure System Used in Laparoscopic 1st and 2nd Stage Orchiopexy" Innovations That Work, Nov. 2002.
Koyle et al., "Laparoscopic Palomo Varicocele Ligation in Children and Adolescents" Pediatric Endosurgery & Innovative Techniques, vol. 6, No. 1, 2002.
Dulemba et al. "Use of a Bipolar Electrothermal Vessel Sealer in Laparoscopically Assisted Vaginal Hysterectomy" Sales/Product Literature; Jan. 2004.
Johnson et al. "Evaluation of a Bipolar etectrothermal Vessel Sealing Device in Hemorrhoidectomy" Sales/Product Literature; Jan. 2004.
Int'l Search Report PCT/US98/18640 dated Dec. 17, 1998.
Int'l Search Report PCT/US98/23950 dated Dec. 29, 1998.
Int'l Search Report PCT/US99/24869 dated Feb. 3, 2000.
Int'l Search Report PCT/US01/11218 dated Aug. 3, 2001.
International Search Report PCT/US01/11224 dated Nov. 13, 2001.
Int'l Search Report PCT/US01/11340 dated Aug. 7, 2001.
Int'l Search Report PCT/US01/11420 dated Oct. 8, 2001.
Int'l Search Report PCT/US02/01890 dated Jul. 17, 2002.
Int'l Search Report PCT/US02/11100 dated Jul. 9, 2002.
Int'l Search Report PCT/US04/03436 dated Oct. 5, 2004.
Int'l Search Report PCT/US04/13273 dated Nov. 22, 2004.
Int'l Search Report PCT/US04/15311 dated Nov. 18, 2004.
Int'l Search Report EP 98944778 dated Oct. 31, 2000.
Int'l Search Report EP 98958575.7 dated Sep. 20, 2002.
Int'l Search Report EP 04027314 dated Mar. 10, 2005.
Int'l Search Report EP 04027479 dated Mar. 8, 2005.
Int'l Search Report EP 04027705 dated Feb. 3, 2005.
Int'l Search Report EP 05013463.4 dated Sep. 28, 2005.
Int'l Search Report EP 05019130.3 dated Oct. 18, 2005.
Int'l Search Report EP 05020665.5 dated Feb. 16, 2006.
Int'l Search Report EP 05020666.3 dated Feb. 17, 2006.
Int'l Search Report EP 05021779.3 dated Jan. 18, 2006.
Int'l Search Report EP 05021197.8 dated Jan. 31, 2006.
Int'l Search Report EP 05021937.7 dated Jan. 13, 2006.
Int'l Search Report—extended—EP 05021937.7 dated Mar. 6, 2006.
Int'l Search Report EP 05023017.6 dated Feb. 16, 2006.
Int'l Search Report EP 05021780.1 dated Feb. 9, 2006.
Int'l Search Report EP 06002279.5 dated Mar. 22, 2006.
Int'l Search Report EP 04 752343.6 dated Jul. 20, 2007.
Int'l Search Report EP 06 024122.1 dated Mar. 19, 2007.
Int'l Search Report EP 07 001480.8 dated Apr. 12, 2007.
Int'l Search Report EP 07 001488.1 dated May 29, 2007.
Int'l Search Report—Extended EP 07 009029.5 dated Jul. 12, 2007.
Int'l Search Report EP 07 009321.6 dated Aug. 17, 2007.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Crouch et al. "A Velocity-Dependent Model for Needle Insertion in Soft Tissue" MICCAI 2005; LNCS 3750 pp. 624-632, Dated: 2005.
Int'l Search Report EP 98957771 dated Aug. 9, 2001.
Int'l Search Report EP 05002671.5 dated Dec. 22, 2008.
Int'l Search Report EP 05002674.9 dated Jan. 16, 2009.
Int'l Search Report EP 05019429.9 dated May 6, 2008.
Int'l Search Report EP 06008515.6 dated Jan. 8, 2009.
Int'l Search Report EP 07 014016 dated Jan. 28, 2008.
Int'l Search Report EP 07 021646.0 dated Jul. 9, 2008.
Int'l Search Report EP 07 021647.8 dated May 2, 2008.
Int'l Search Report EP 08 02692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 09 152267.2 Dated Jun. 15, 2009.
Int'l Search Report EP 09 152898.4 Dated Jun. 10, 2009.
Int'l Search Report PCT/US98/24281 dated Feb. 22, 1999.
Int'l Search Report PCT/US03/28534 dated Dec. 19, 2003.
Int'l Search Report PCT/US07/021438 dated Apr. 1, 2008.
Int'l Search Report PCT/US07/021440 dated Apr. 8, 2008.
Int'l Search Report PCT/US08/61498 dated Sep. 22, 2008.
Int'l Search Report PCT/US09/032690 dated Jun. 16, 2009.

* cited by examiner

SYSTEM AND METHOD FOR CONTROLLING ELECTRODE GAP DURING TISSUE SEALING

BACKGROUND

1. Technical Field

The present disclosure relates to an electrosurgical instrument and method for performing electrosurgical procedures. More particularly, the present disclosure relates to an open or endoscopic bipolar electrosurgical forceps that includes opposing jaw members each having a sealing plate for grasping tissue and supplying electrosurgical energy thereto. The pressure exerted by the sealing plates on the tissue is adjusted using a feedback control loop that utilizes gap distance between the sealing plates as a control variable.

2. Background of Related Art

Electrosurgery involves application of high radio frequency electrical current to a surgical site to cut, ablate, coagulate, cauterize, desiccate or seal tissue. Tissue or vessel sealing is a process of liquefying the collagen, elastin and ground substances in the tissue so that they reform into a fused mass with significantly-reduced demarcation between the opposing tissue structures. Cauterization involves the use of heat to destroy tissue and coagulation is a process of desiccating tissue wherein the tissue cells are ruptured and dried.

In bipolar electrosurgery, one of the electrodes of the hand-held instrument functions as the active electrode and the other as the return electrode. The return electrode is placed in close proximity to the active electrode such that an electrical circuit is formed between the two electrodes (e.g., electrosurgical forceps). In this manner, the applied electrical current is limited to the body tissue positioned between the electrodes. When the electrodes are sufficiently separated from one another, the electrical circuit is open and thus inadvertent contact with body tissue with either of the separated electrodes does not cause current to flow.

A forceps is a pliers-like instrument that relies on mechanical action between its jaws to grasp, clamp and constrict vessels or tissue. So-called "open forceps" are commonly used in open surgical procedures whereas "endoscopic forceps" or "laparoscopic forceps" are, as the name implies, are used for less invasive endoscopic surgical procedures. Electrosurgical forceps (open or endoscopic) utilize mechanical clamping action and electrical energy to effect hemostasis on the clamped tissue. The forceps includes electrosurgical sealing plates that apply the electrosurgical energy to the clamped tissue. By controlling the intensity, frequency and duration of the electrosurgical energy applied through the sealing plates to the tissue, the surgeon can coagulate, cauterize and/or seal tissue.

Tissue sealing procedures involve more than simply cauterizing tissue. In order to affect a proper seal in vessels or tissue, it has been determined that a variety of mechanical and electrical parameters must be accurately controlled: the pressure applied to the tissue; the gap distance between the electrodes (i.e., distance between opposing jaw members when closed about tissue); and amount of energy applied to tissue.

Numerous electrosurgical instruments have been proposed in the past for various open and endoscopic surgical procedures. However, most of these instruments cauterize or coagulate tissue and are not designed to create an effective or a uniform seal. Other instruments generally rely on clamping pressure alone to procure proper sealing thickness and are often not designed to take into account gap tolerances and/or parallelism and flatness requirements, which are parameters that, if properly controlled, can assure a consistent and effective tissue seal.

SUMMARY

The present disclosure relates to a vessel or tissue sealing instrument that is designed to manipulate, grasp and seal tissue utilizing jaw members. According to one aspect of the present disclosure, an electrosurgical system for sealing tissue is disclosed that includes an electrosurgical forceps. The forceps includes a drive rod and an end effector assembly coupled to the drive rod at a distal end thereof. The end effector assembly includes jaw members wherein longitudinal reciprocation of the drive rod moves the jaw members from a first position in spaced relation relative to one another to a subsequent position wherein the jaw members cooperate to grasp tissue therebetween. Each of the jaw members includes a sealing plate that communicates electrosurgical energy through tissue held therebetween. The jaw members are adapted to connect to an electrosurgical generator. The system also includes one or more sensors that determine a gap distance between the sealing plates of the jaw members and a pressure applicator coupled to the drive rod. The pressure applicator is configured to move the drive rod in a longitudinal direction. The system further includes a controller adapted to communicate with the sensors and to control the pressure applicator in response to the determined gap distance during the sealing process.

The present disclosure also relates to a method for sealing tissue including the step of providing an electrosurgical forceps for sealing tissue. The forceps having at least one shaft member having a drive rod and an end effector assembly mechanically coupled to the drive rod at a distal end thereof. The end effector assembly includes jaw members wherein longitudinal reciprocation of the drive rod moves the jaw members from a first position in spaced relation relative to one another to a subsequent position wherein the jaw members cooperate to grasp tissue therebetween. Each of the jaw members includes a sealing plate that communicates electrosurgical energy through tissue held therebetween. The jaw members are adapted to connect to an electrosurgical generator. The method also includes the steps of providing a controller having a pressure applicator mechanically coupled to the drive rod and configured to move the drive rod in a longitudinal direction as well as grasping tissue between the sealing plates and measuring a gap distance between the sealing plates. The method further includes the step of controlling a pressure applicator as a function of the measured gap distance.

BRIEF DESCRIPTION OF THE DRAWINGS

Various embodiments of the present disclosure are described herein with reference to the drawings wherein.

DETAILED DESCRIPTION

Particular embodiments of the present disclosure are described hereinbelow with reference to the accompanying drawings. In the following description, well-known functions or constructions are not described in detail to avoid obscuring the present disclosure in unnecessary detail. Those skilled in the art will understand that the invention according to the present disclosure may be adapted for use with either monopolar or bipolar electrosurgical system.

The present disclosure provides for an apparatus, system and method of controlling pressure exerted by opposing jaw members on tissue grasped therebetween during sealing. Since tissue thickness corresponds to the gap distance "G" between opposing jaw members, it is envisioned that adjusting the pressure exerted on the tissue based on the desired rate of change of the gap distance "G" controls the decrease in the tissue thickness during the sealing process resulting in a confident, more reliable tissue seal. In other words, controlling the rate at which the thickness of the tissue decreases is beneficial in creating a strong seal since the optimum amount of tissue remains enclosed between the opposing jaw members.

Figure 1A:
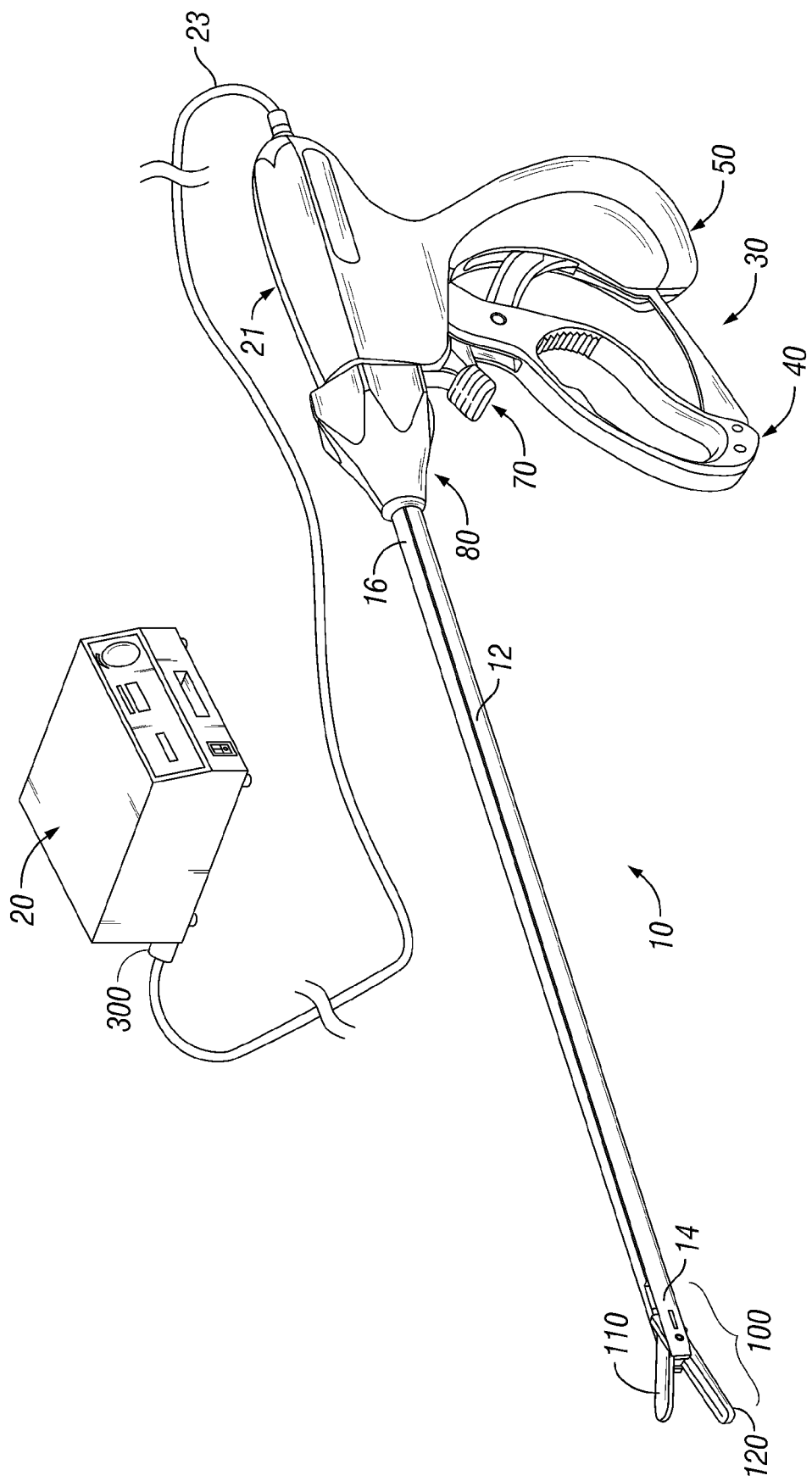
FIG. 1A is a perspective view of an electrosurgical system according to one embodiment of the present disclosure.

FIG. 1A shows an electrosurgical system having an endoscopic vessel sealing bipolar forceps 10 electrically coupled to an electrosurgical generator 20 that is adapted to supply electrosurgical high radio frequency (RF) energy thereto. The forceps 10 is shown by way of example and other suitable electrosurgical forceps are also envisioned that allow control of RF output to provide a reliable seal. Those skilled in the art will understand that the invention according to the present disclosure may be adapted for use with either an endoscopic instrument or an open instrument.

It should also be appreciated that different electrical and mechanical connections and other considerations apply to each particular type of instrument. However, the novel aspects with respect to controlling pressure as a function of the gap distance "G" and the operating characteristics of the instruments remain generally consistent with respect to both the open or endoscopic designs.

Figure 1B:
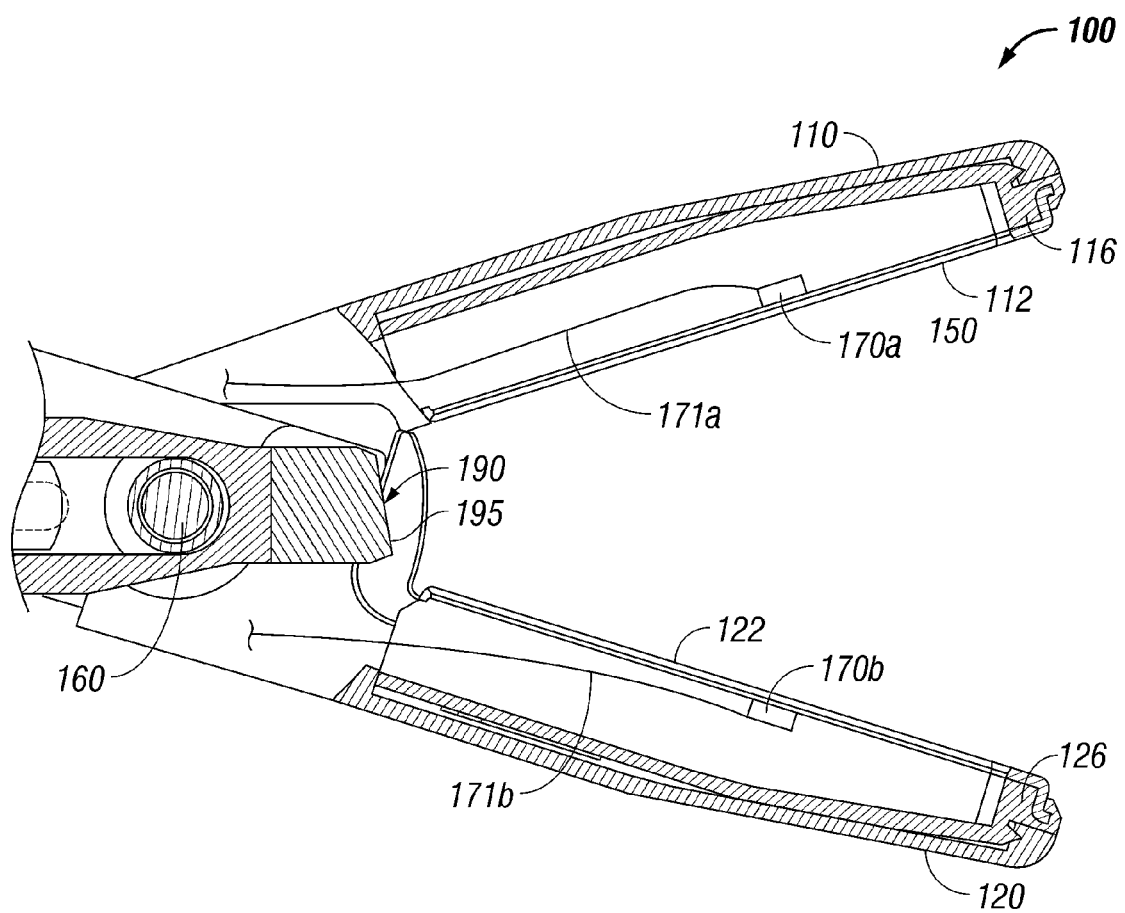
FIG. 1B is a side, partial internal view of an end effector assembly of an endoscopic forceps according to one embodiment of the present disclosure.

FIGS. 1A-1B show the forceps 10 that is configured to support an end effector assembly 100 at a distal end thereof. More particularly, forceps 10 generally includes a housing 21, a handle assembly 30, a rotating assembly 80, and a trigger assembly 70 that mutually cooperate with the end effector assembly 100 to grasp, seal and, if desired, divide tissue.

The forceps 10 also includes a shaft 12 that has a distal end 14 that mechanically engages the end effector assembly 100 and a proximal end 16 that mechanically engages the housing 21 proximate the rotating assembly 80. In the drawings and in the description that follows, the term "proximal", refers to the end of the forceps 10 that is closer to the user, while the term "distal" refers to the end of the forceps that is further from the user.

Figure 2:
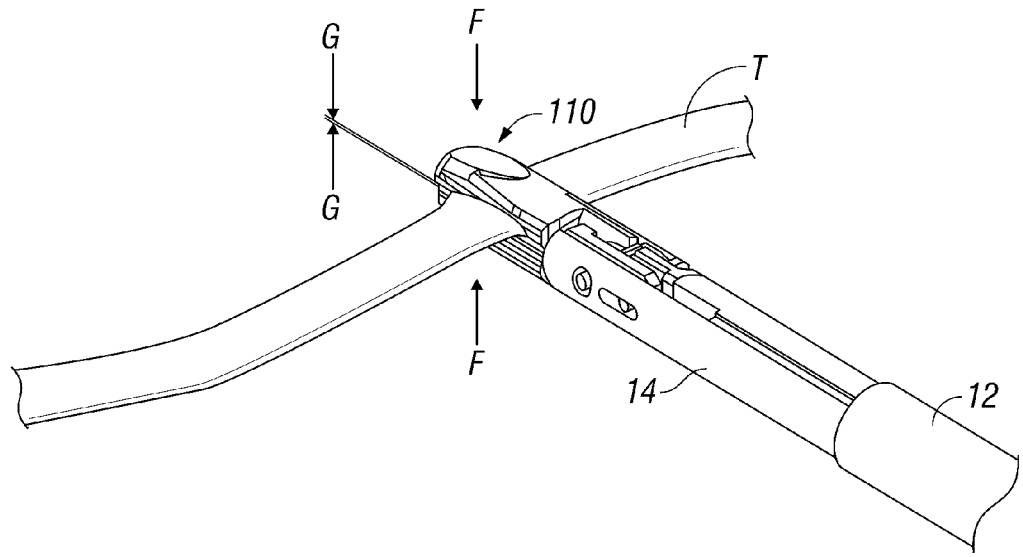
FIG. 2 is a rear, perspective view of the end effector of FIG. 1B shown with tissue grasped therein.

The forceps 10 also includes a plug 300 that connects the forceps 10 to a source of electrosurgical energy, e.g., the electrosurgical generator 20, via an electrical cable 23. Handle assembly 30 includes a fixed handle 50 and a movable handle 40. Handle 40 moves relative to the fixed handle 50 to actuate the end effector assembly 100 and enables a user to grasp and manipulate tissue "T" as shown in FIG. 2.

The generator 20 includes input controls (e.g., buttons, activators, switches, touch screen, etc.) for controlling the generator 20. In addition, the generator 20 may include one or more display screens for providing the surgeon with a variety of output information (e.g., intensity settings, treatment complete indicators, etc.). The controls allow the surgeon to adjust the RF energy, waveform, and other parameters to achieve the desired waveform suitable for a particular task (e.g., coagulating, tissue sealing, intensity setting, etc.). The forceps 10 may also include a plurality of input controls that may be redundant with certain input controls of the generator 20. Placing the input controls at the forceps 10 allows for easier and faster modification of RF energy parameters during the surgical procedure without requiring interaction with the generator 20.

Figure 3:
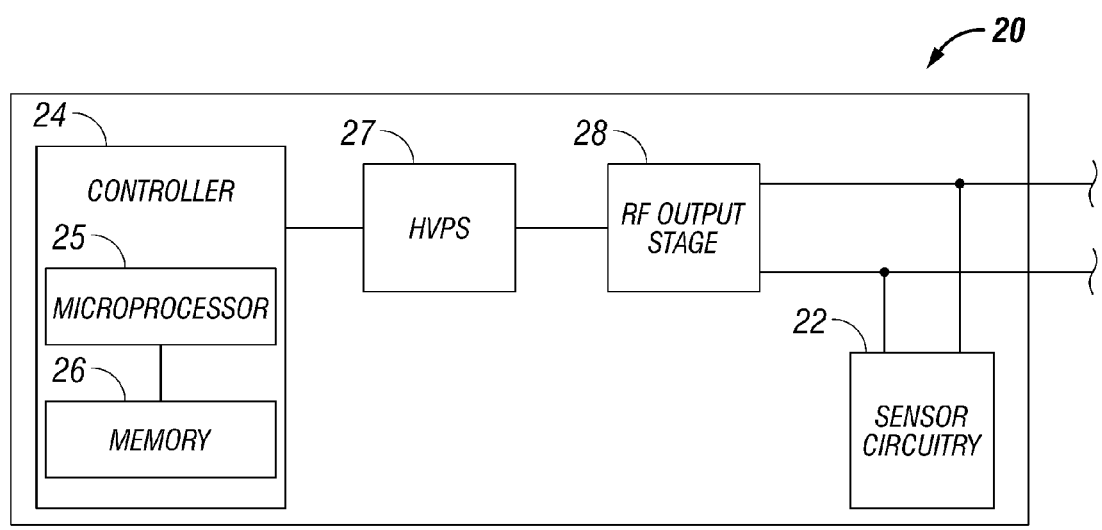
FIG. 3 is a schematic block diagram of a generator system according to one embodiment of the present disclosure.

FIG. 3 shows a schematic block diagram of the generator 20 having a controller 24, a high voltage DC power supply 27 ("HVPS") and an RF output stage 28. The HVPS 27 provides high voltage DC power to RF output stage 28, which then converts high voltage DC power into RF energy and delivers the RF energy to an active electrode. In particular, the RF output stage 28 generates sinusoidal waveforms of high frequency RF energy. The RF output stage 28 is configured to generate a plurality of suitable waveforms having various duty cycles, peak voltages, crest factors, and other parameters. Certain types of waveforms are suitable for specific electrosurgical modes. For instance, the RF output stage 28 generates a 100% duty cycle sinusoidal waveform in a so called "cut mode," which is best suited for dissecting tissue and a 25% duty cycle waveform in a so called "coagulation mode," which is best used for cauterizing tissue to stop bleeding.

The controller 24 includes a microprocessor 25 connected to a memory 26, which may be volatile type memory (e.g., RAM) and/or non-volatile type memory (e.g., flash media, disk media, etc.). The microprocessor 25 includes an output port that is connected to the HVPS 27 and/or RF output stage 28 allowing the microprocessor 25 to control the output of the generator 20 according to either open and/or closed control loop schemes.

The sensor circuitry 22 may include a plurality of sensors for measuring a variety of tissue and/or energy properties (e.g., tissue impedance, tissue temperature, output current and/or voltage, gap distance, etc.). The sensor circuitry 22 is also connected to sensors 170a and 170b, which measure the gap distance "G" between the opposing jaw members 110 and 120 (FIG. 1B). Such sensors are within the purview of those skilled in the art. A closed loop control scheme is a feedback control loop wherein sensor circuitry 22 provides feedback to the controller 24. The controller 24 signals the HVPS 27 and/or RF output stage 28, which then adjusts the output of DC and/or RF energy, respectively. The sensor circuitry 22 also transmits measured gap distance "G" information to the controller 24, which then adjusts the pressure exerted by the opposing jaw members 110 and 120 exerted on the tissue grasped therein. The controller 24 also receives input signals from the input controls of the generator 20 or the forceps 10. The controller 24 utilizes the input signals to adjust power outputted by the generator 20 and/or performs other suitable control functions thereon.

With references to FIGS. 1A-1B, the end effector assembly 100 includes a pair of opposing jaw members 110 and 120 each having an electrically conductive sealing plate 112 and 122, respectively, attached thereto for conducting electrosurgical energy through tissue "T" held therebetween. More particularly, the jaw members 110 and 120 move in response to movement of the handle 40 from an open position to a closed position. In open position the sealing plates 112 and 122 are disposed in spaced relation relative to one another. In a clamping or closed position the sealing plates 112 and 122 cooperate to grasp tissue and apply electrosurgical energy thereto.

The jaw members 110 and 120 are activated using a drive assembly (not explicitly shown) enclosed within the housing 21. The drive assembly cooperates with the movable handle 40 to impart movement of the jaw members 110 and 120 from the open position to the clamping or closed position. Examples of handle assemblies are shown and described in commonly-owned U.S. application Ser. No. 10/369,894 entitled "VESSEL SEALER AND DIVIDER AND METHOD MANUFACTURING SAME" and commonly owned U.S. application Ser. No. 10/460,926 entitled "VESSEL SEALER AND DIVIDER FOR USE WITH SMALL TROCARS AND CANNULAS".

In addition, the handle assembly 30 of this particular disclosure may include a four-bar mechanical linkage, which provides a unique mechanical advantage when sealing tissue between the jaw members 110 and 120. For example, once the desired position for the sealing site is determined and the jaw members 110 and 120 are properly positioned, handle 40 may be compressed fully to lock the electrically conductive sealing plates 112 and 122 in a closed position against the tissue. Movable handle 40 of handle assembly 30 is ultimately connected to a drive rod 32 that, together, mechanically cooperate to impart movement of the jaw members 110 and 120 from an open position wherein the jaw members 110 and 120 are disposed in spaced relation relative to one another, to a clamping or closed position wherein the jaw members 110 and 120 cooperate to grasp tissue therebetween.

Figure 1C:
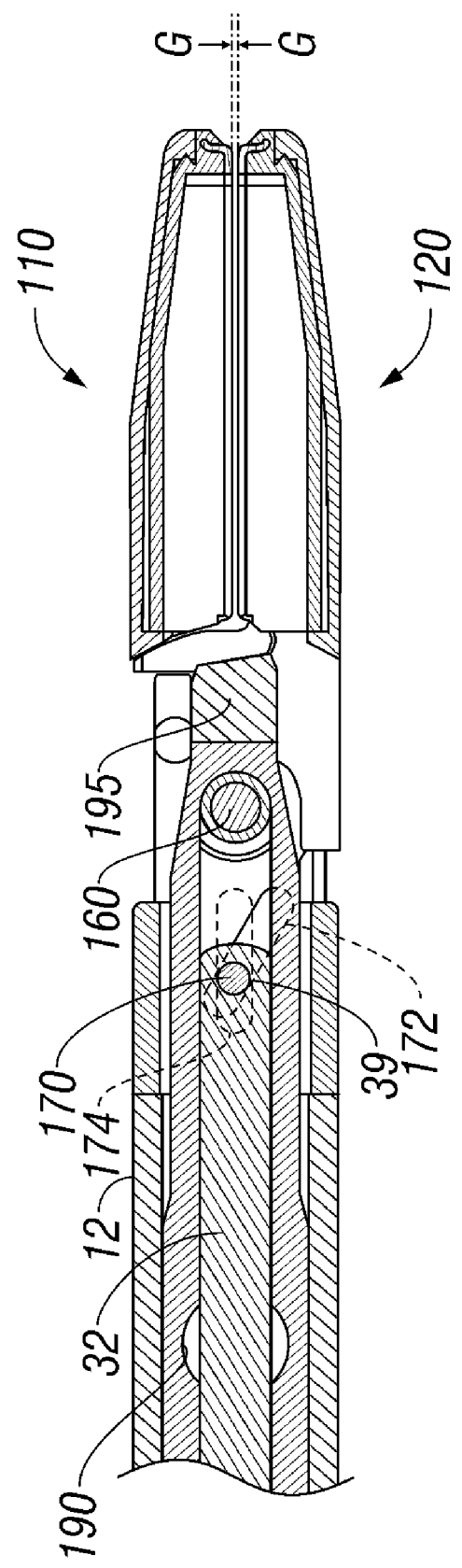
FIGS. 1C-1E are side, partial internal views of an end effector assembly of FIG. 1B with pressure application mechanisms according to various embodiments of the present disclosure.

As best illustrated in FIG. 1C, drive rod 32 includes a pin slot 39 disposed at the distal tip of the drive rod 32 and dimensioned to house the cam pin 170 such that longitudinal reciprocation of the drive rod 32 translates the cam pin 170, which, in turn, rotates the jaw members 110 and 120 about pivot pin 160. The cam pin 170 rides within slots 172 and 174 of the jaw members 110 and 120, respectively, which causes the jaw members 110 and 120 to rotate from the open to closed positions about the tissue. In particular, as the drive rod 32 is pulled proximally the cam pin 170 is moved proximally within cam slots 172 and 174 and closes the jaw members 110 and 120 relative to one another. The drive rod 32 is configured to be actuated via the handle 40 and/or other suitable pressure application mechanisms.

Figure 1D:
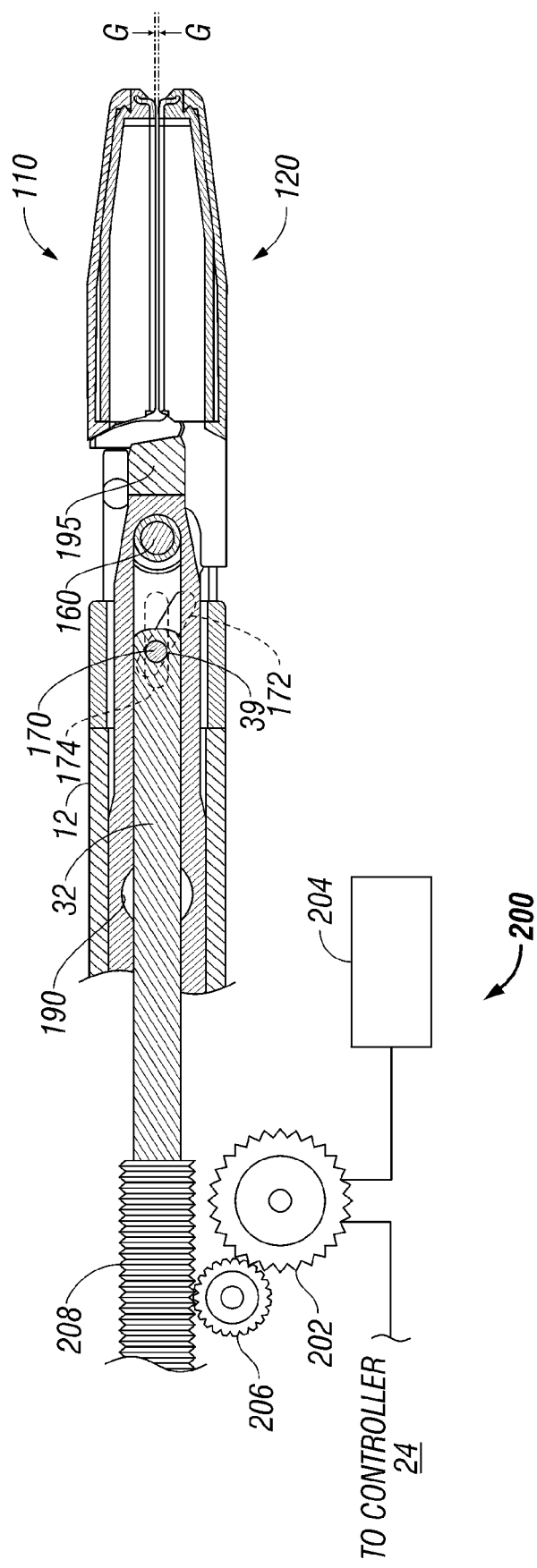

FIG. 1D shows a motor-controlled pressure applicator 200 that includes an electric motor 202 powered by a power source 204. The power source 204 may either be a stand-alone low voltage DC source (e.g., battery) or an integrated low-voltage power source as part of the HVPS 27. The drive rod 32 includes a threaded portion 208 that is in mechanical communication with the motor 202. In particular, the motor 202 includes a gear box 206 that is mechanically coupled to the threaded portion 208 so that when the motor 202 is activated, the gears of the gear box 206 rotate and thereby longitudinally move the drive rod 32. Pulling the drive rod 32 proximally and moving the jaw members 110 and 120 apart or pushing the drive rod 32 distally and moving the jaw members 110 and 120 together is accomplished by varying the direction of rotation of the motor 202. The rate of closure of the jaw members 110 and 120 is controlled by varying the gears within the gear box 208 and/or the power supplied to the motor 202, which, in turn, adjusts the rate of rotation and torque exerted on the drive rod 32. Control of the motor 202 is achieved via the controller 24, which automatically adjusts the operating parameters thereof based on user input or sensed feedback from the sensor circuitry 22 and/or the sensors 170a and 170b.

Figure 1E:
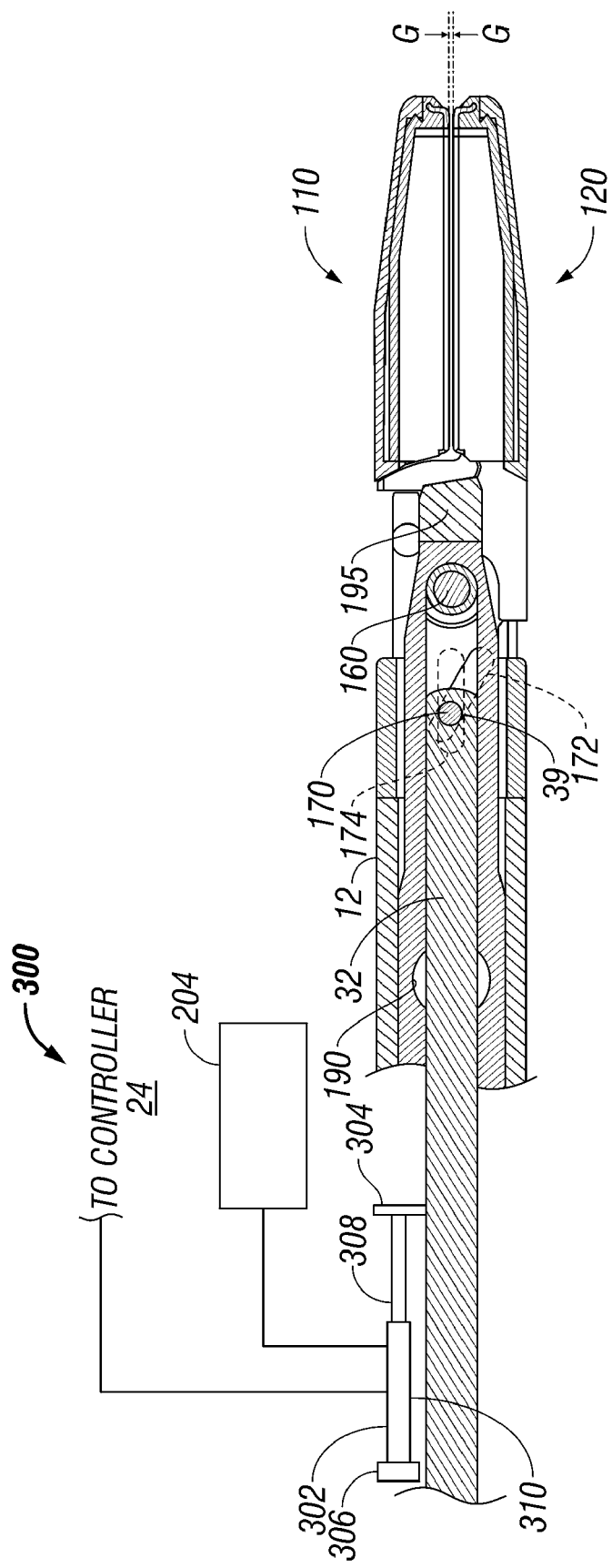

FIG. 1E shows another embodiment of a pressure applicator 300 that includes a linear actuator 302 powered by the power source 204. The linear actuator 302 includes a housing cylinder 310 and a shaft 308. The shaft 208 is mechanically coupled to the to the drive rod 32 at an interface 304 and the housing cylinder 310 is mechanically coupled to the interior wall of the housing 21 at an interface 306. The linear actuator 302 moves the drive rod 32 in a longitudinal direction proximally or distally by expanding or contracting, respectively, between the interfaces 304 and 306. The linear actuator 302 includes either an electric motor or a pneumatic or hydraulic cylinders that extend or retract the shaft 308. Those skilled in the art will readily appreciate that if the linear actuator 302 is pneumatic, the shaft 308 may be part of the pneumatic cylinder. The power source 204 is connected to the linear actuator 302 and provides electrical power thereto. The controller 24 controls the operating parameters of the linear actuator 302 either directly or by controlling the power source 202 based on user input or sensed feedback from the sensor circuitry 22 and/or the sensors 170a and 170b.

The pressure applicators 200 and 300 may be housed within the housing 21 or outside thereof along the shaft 12 to enable the pressure applicators 200 and 300 to interface with drive rod 32.

The details relating to the inter-cooperative relationships of the inner-working components of forceps 10 are disclosed in the above-cited commonly-owned U.S. patent application Ser. No. 10/369,894. Another example of an endoscopic handle assembly that discloses an off-axis, lever-like handle assembly, is disclosed in the above-cited U.S. patent application Ser. No. 10/460,926.

Referring back to FIGS. 1A-1B, the forceps 10 also includes a trigger 70 that advances a knife 190 disposed within the end effector assembly 100. Once a tissue seal is formed, the user optionally activates the trigger 70 to separate the tissue "T" along the tissue seal. Knife 190 preferably includes a sharpened edge 195 for severing the tissue "T" held between the jaw members 110 and 120 at the tissue sealing site. The knife 190 longitudinally reciprocates in a longitudinally-oriented channel (not explicitly shown) defined in the conductive sealing plates 112 and 122 extending from the proximal end to the distal end thereof. The channel facilitates longitudinal reciprocation of the knife 190 along a preferred cutting plane to effectively and accurately separate the tissue "T" along a formed tissue seal.

The forceps 10 also includes a rotating assembly 80 mechanically associated with the shaft 12 and the drive assembly (not explicitly shown). Movement of the rotating assembly 80 imparts similar rotational movement to the shaft 12, which, in turn, rotates the end effector assembly 100. Various features along with various electrical configurations for the transference of electrosurgical energy through the handle assembly 20 and the rotating assembly 80 are described in more detail in the above-mentioned commonly-owned U.S. patent application Ser. Nos. 10/369,894 and 10/460,926.

As best seen with respect to FIGS. 1A-1B, the end effector assembly 100 attaches to the distal end 14 of shaft 12. The jaw members 110 and 120 are preferably pivotable about a pivot 160 from the open to closed positions upon relative reciprocation, i.e., longitudinal movement, of the drive assembly (not explicitly shown). Again, mechanical and cooperative relationships with respect to the various moving elements of the end effector assembly 100 are further described by example with respect to the above-mentioned commonly-owned U.S. patent application Ser. Nos. 10/369,894 and 10/460,926.

The forceps 10 may be designed such that it is fully or partially disposable depending upon a particular purpose or to achieve a particular result. For example, end effector assembly 100 may be selectively and releasably engageable with the distal end 14 of the shaft 12 and/or the proximal end 16 of the shaft 12 may be selectively and releasably engageable with the housing 21 and handle assembly 30. In either of these two instances, the forceps 10 may be either partially disposable or reposable, such as where a new or different end effector assembly 100 or end effector assembly 100 and shaft 12 are used to selectively replace the old end effector assembly 100 as needed.

Since the forceps 10 applies energy through electrodes, each of the jaw members 110 and 120 includes an electrically conductive sealing plate 112 and 122, respectively, disposed on an inner-facing surface thereof. Thus, once the jaw members 110 and 120 are fully compressed about the tissue T, the forceps 10 is now ready for selective application of electrosurgical energy as shown in FIG. 2. At that point, the electrically conductive plates 112 and 122 cooperate to seal tissue "T" held therebetween upon the application of electrosurgical energy. Jaw members 110 and 120 also include insulators 116 and 126, which together with the outer, non-conductive plates of the jaw members 110 and 120 are configured to limit and/or reduce many of the known undesirable effects related to tissue sealing, e.g., flashover, thermal spread and stray current dissipation as shown in FIG. 1B.

The gap distance "G" is used as a sensed feedback to control the thickness of the tissue being grasped. More particularly, a pair of opposing sensors 170a and 170b are configured to provide real-time feedback relating to the gap distance between the sealing plates 112 and 122 of the jaw members 110 and 120 during the sealing process via electrical connection 171a and 171b, respectively. The sensors 170a and 170b provide sensed feedback to the sensor circuitry 22, which then signals the controller 24. The controller 24 then signals the pressure applicator to adjust the pressure applied to the tissue based on the measured gap distance "G." Consequently, this controls the rate at which tissue grasped between the sealing plates 112 and 122 is being compressed.

The sensors 170a and 170b may be any suitable sensors, such as laser distancers, LED distancers, optical encoders, and the like. The laser and LED distancers operate by bouncing light beams from an opposing surface and measuring the duration of the beam of light to travel back to the sensors 170a and 170b. The sensors 170a and 170b bounce light beams from the opposing surfaces (e.g., sealing plates 112 and 122). Each of the sensors 170a and 170b provides an individual measurement of the distance between the jaw members 110 and 120. An optical encoder (e.g., a linear encoder) is a sensor paired with a scale (not explicitly shown) that corresponds to a particular position of the jaw members 110 and 120. The sensor 170a reads the scale and converts the encoded position into an analog or digital signal, which can then be decoded into position by a digital readout (e.g., sensor circuitry 22). Motion of the jaw members 110 and 120 is determined by change in position over time. Linear encoder technologies include capacitive, inductive, eddy current, magnetic, and optical. Optical technologies include shadow, self imaging and interferometric. The sensor circuitry 22 and/or the controller 24 then average the result to arrive at the gap distance "G" separating the jaw members 110 and 120. The sensor circuitry 22 and/or the controller 24 may perform various other types of calculations based on the gap distance "G" measurements to obtain desired empirical values for sensed feedback control.

The sensors 170a and 170b may also be configured to measure suitable tissue properties, such as tissue impedance and temperature. Such sensors are within purview of those skilled in the art.

The gap distance "G" is directly related to the thickness of tissue being grasped between the sealing plates 112 and 122. Therefore, the thickness of tissue being grasped may be controlled based on the gap distance "G." As shown in a graph of FIG. 5, thickness of the tissue (and therefore the gap distance "G") decreases as pressure and energy are applied thereto. Tissue thickness decreases for at least two reasons. First, the pressure applied to the tissue by the sealing plates 112 and 122 compresses tissue. Second, RF energy applied to the tissue increases the temperature therein at which point intracellular fluids being to boil thereby causing the cells to rupture uncontrollably.

Figure 5:
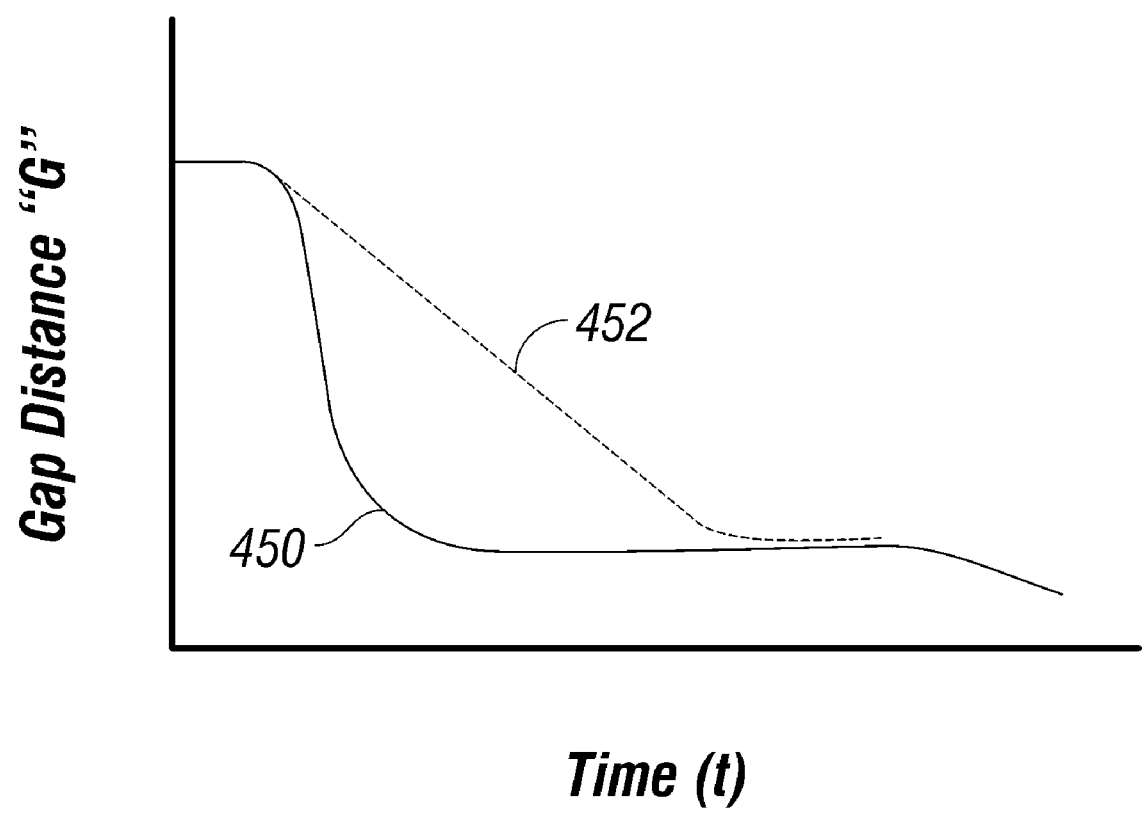
FIG. 5 shows a graph of gap distance "G" versus time (t) utilizing the method of FIG. 4.

The graph of FIG. 5 shows a plot 450 of gap distance "G" between electrode plates of a conventional electrosurgical sealing forceps where RF energy is supplied at a constant rate and pressure is unregulated. In the plot 450, the gap distance "G" falls to approximately half of the original value very quickly (e.g., approximately 0.5 seconds). This demonstrates as pressure and energy are applied at a constant rate during initial stages of a sealing procedure, thickness of the tissue rapidly decreases as the tissue is being cooked.

Plot 452 shows a more desirable progression of the gap distance "G." In particular, if the thickness of the tissue decreases at a more controlled rate the mucosa and submucosa tissues remain in the seal area. Conventionally, the mucosa and submucosa layers are pressed out of the seal area due to uncontrolled delivery of RF energy, resulting in a less secure seal. Therefore, the controlled decrease of the gap distance "G" of the plot 452 allows for controlled decreases of the tissue thickness. This may be accomplished by controlling pressure as a function of the gap distance "G." More specifically, an embodiment of the present disclosure controls application of pressure to tissue during sealing based on the gap distance "G" to maintain the desired rate of cell rupture, thereby controlling the thickness of the tissue being grasped.

Figure 4:
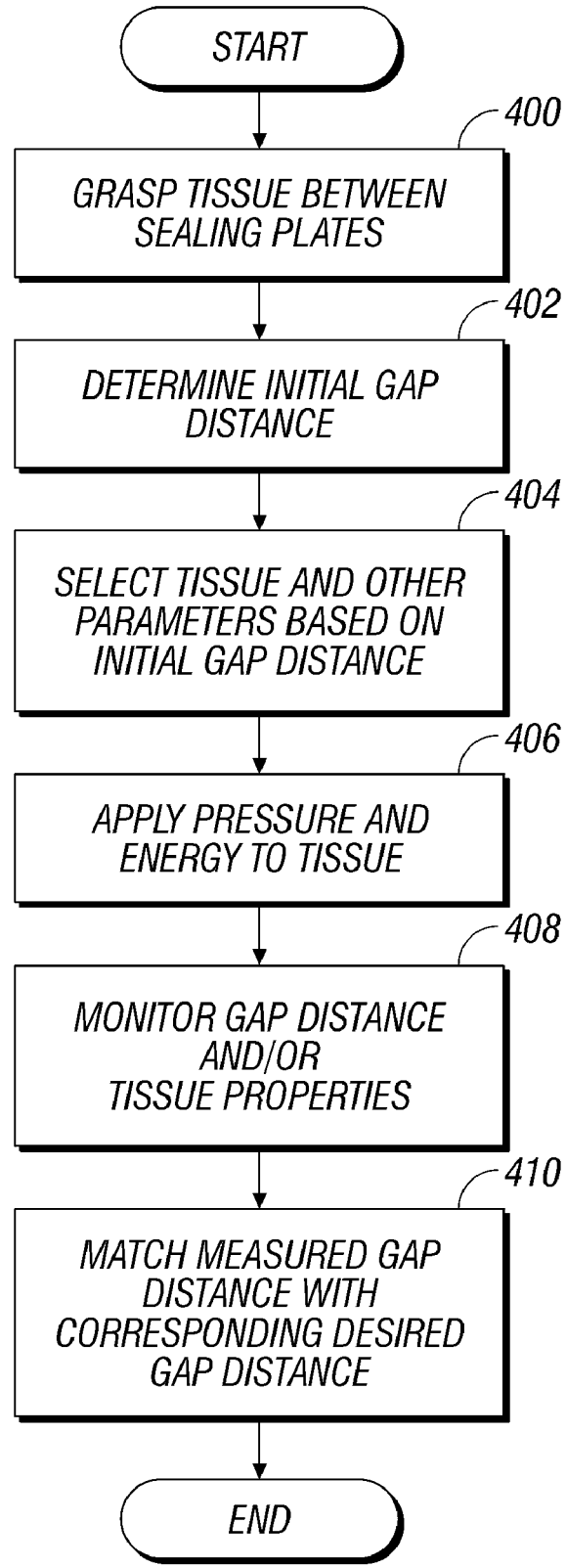
FIG. 4 is a flowchart showing a sealing method using a bipolar forceps according to a method of the present disclosure.

A sealing method according to one embodiment of the present disclosure is shown in FIG. 4. In step 400, the forceps 10 grasps the tissue "T" using the jaw members 110 and 120. The sealing plates 112 and 122 are activated and are in contact with the tissue "T" but are not fully closed. When the sealing plates 112 and 122 contact the tissue "T" electrosurgical energy is applied thereto and the collagen contained therein is denatured and becomes more mobile (i.e., liquefies).

In step 402, initial gap distance "G" is determined by sensors 170a, 170b, which measure the distance between jaw members 110 and 120. The initial gap distance "G" measurement is useful in determining the thickness of the tissue being grasped. The thickness is particularly important since various adjustments to the procedure may be made based on relative tissue thickness. For instance, thin tissue types (e.g., small blood vessels) may require a certain amount of energy and pressure to properly seal desiccation whereas thicker tissue types may require more pressure and more energy. Other tissue parameters may be used to determine thickness and/or properties of the tissue. A second sensor or one of the sensors

170a and 170b may be adapted to measure boundary conditions, jaw fill, hydration. This may be accomplished by using optical sensors adapted to measure opacity of the tissue. The tissue property measurements are transmitted to the controller 24 through the sensor circuitry 22, wherein adjustments to the generator 20 and the pressure applicator are made in real-time based on the measurements.

In step 404, energy, tissue and other treatment parameters are selected. More specifically, the initial gap distance "G" measurement is transmitted to the controller 24 where the tissue thickness is determined as a function thereof. The determination may be accomplished by matching the measured initial gap distance "G" with gap distance "G" values stored in a look-up table stored in memory 26. The look-up table may include a plurality of gap distance "G" values and corresponding tissue thickness values. Upon finding a match, corresponding tissue thickness is obtained. In addition, the look-up table may also include suitable energy and pressure parameters associated with the corresponding tissue thickness. Energy and pressure parameters may also be loaded based on the initial gap distance "G" determination without determining the tissue thickness.

In step 406, the forceps 10 begins to apply pressure and energy to the tissue "T" using the jaw members 110 and 120 based on the energy and pressure parameters loaded in step 504. The pressure may be constant or be applied to according to a desired pattern (e.g., a control curve). The desired gap distance "G" may be expressed as a desired gap distance "G" trajectory, namely, plot 452. The gap distance trajectory "G" includes a plurality of desired gap distance "G" values. The look-up table may include a plurality of parameters, such as starting and ending gap distances "G," desired slope(s), etc. The microprocessor 25 uses these parameters to construct the plot 452 (i.e., the desired trajectory), which may be linear, quasi-linear, or non-linear. The gap distance "G" may also be controlled according to preset parameters and time increments based on pre-existing empirical data and not in real-time according to real changes in gap distance "G."

In step 408, as RF energy and pressure are applied to tissue, gap distance "G" is continually monitored and compared with the plot 452 in particular with corresponding desired gap distance "G" values. The gap distance "G" may also be controlled based in response to other tissue properties, such as tissue impedance and temperature. Impedance and temperature are continually monitored along with the gap distance "G" and are transmitted by the sensors 170a and 170b to the controller 24 wherein the controller 24 makes appropriate adjustments to the pressure applicator to control the pressure.

In step 410, the controller 24 adjusts the pressure based on the measured gap distance "G" or other tissue properties by matching measured gap distance "G" with desired gap distance "G." This is accomplished at specific time increments, which may be predetermined or dynamically defined. Namely, for every time increment, measured gap distance "G" is compared with a corresponding desired gap distance "G." If the measured gap distance drops off rapidly and is below the desired corresponding gap distance "G" value of the plot 452, the controller 24 adjusts pressure output of the pressure applicator (e.g., lowers the pressure).

An apparatus and method according to the present disclosure allow for tissue sealing procedures that retain the collagen at the sealing site, which is known to enhance the consistency, effectiveness, and strength of tissue seals. This may be accomplished by using a "slow close" activation to initially denature the collagen and then close the sealing plates under pressure at a predetermined rate. Further details relating to "slow close" activation are disclosed in commonly-owned U.S. application Ser. No. 11/095,123 filed Mar. 31, 2005 entitled "ELECTROSURGICAL FORCEPS WITH SLOW CLOSURE SEALING PLATES AND METHOD OF SEALING TISSUE", which is herein incorporated by reference. This allows for limited extrusion of the cured and mixed collagen mass from the sealing site, which contributes to an effective and uniform seal.

Figure 6:
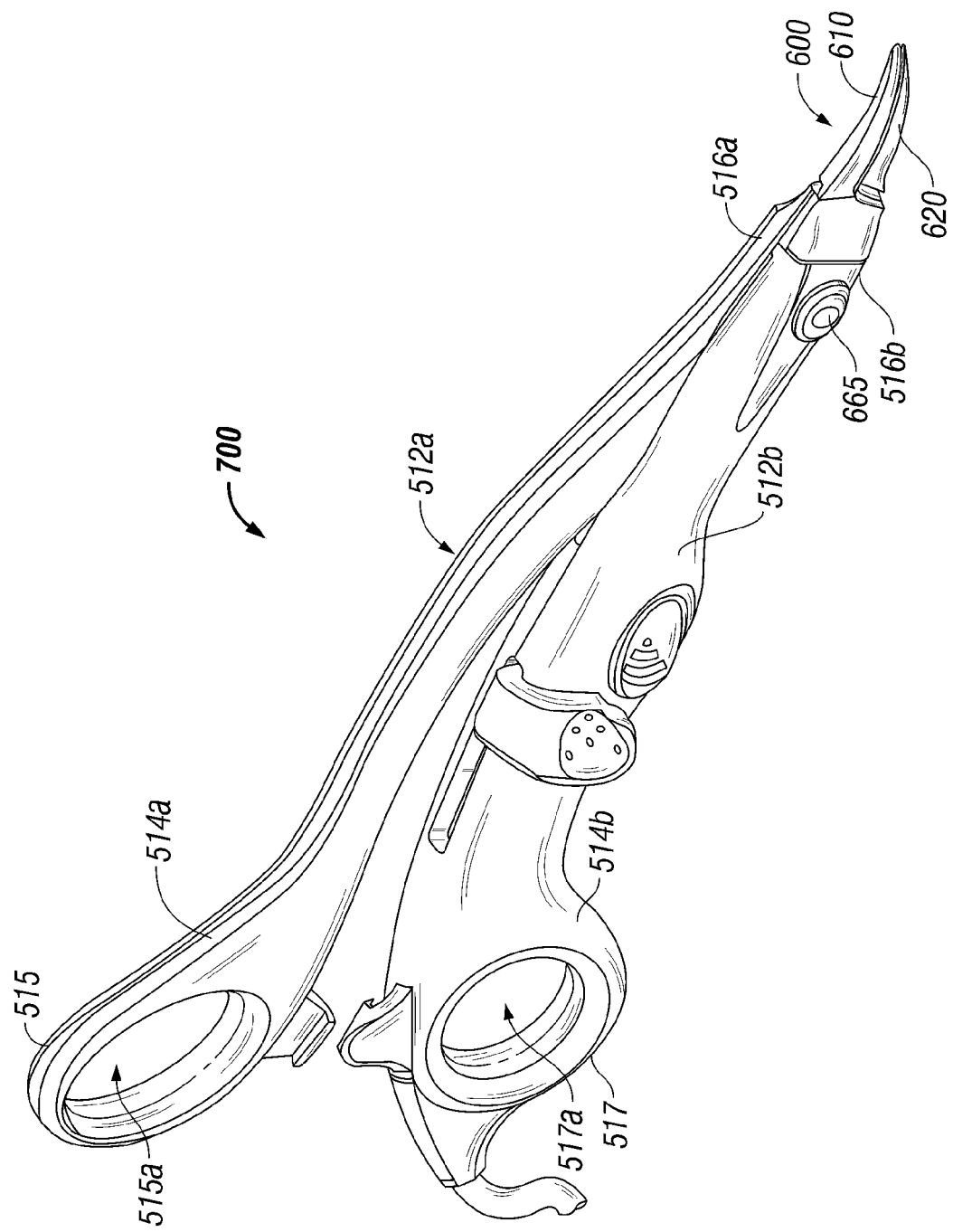
FIG. 6 is a perspective view of an open bipolar forceps that is configured to close at a predetermined rate according to one embodiment of the present disclosure.

From the foregoing and with reference to the various figure drawings, those skilled in the art will appreciate that certain modifications can also be made to the present disclosure without departing from the scope of the same. For example and as mentioned above, any of the slow closure techniques, methods and mechanisms disclosed herein may be employed on an open forceps such as the open forceps 700 disclosed in FIG. 6. The forceps 700 includes an end effector assembly 600 that attaches to the distal ends 516a and 516b of shafts 512a and 512b, respectively. The end effector assembly 600 includes pair of opposing jaw members 610 and 620 that are pivotally connected about a pivot pin 665 and are movable relative to one another to grasp vessels and/or tissue. Stop member assemblies, such as those described with respect to FIGS. 1A-1B, 3 and 4, and sensors 170a and 170b may be disposed within the end effector 600 to regulate the RF energy according to real-time measurements and changes to the gap distance "G" during sealing.

Each shaft 512a and 512b includes a handle 515 and 517, respectively, disposed at the proximal end 514a and 514b thereof each of the handles 515 and 517 define a finger hole 515a and 517a, respectively, therethrough for receiving a finger of the user. Finger holes 515a and 517a facilitate movement of the shafts 512a and 512b relative to one another, which, in turn, pivot the jaw members 610 and 620 from an open position wherein the jaw members 610 and 620 are disposed in spaced relation relative to one another to a clamping or closed position wherein the jaw members 610 and 620 cooperate to grasp tissue or vessels therebetween. Further details relating to one particular open forceps are disclosed in commonly-owned U.S. application Ser. No. 10/962,116 filed Oct. 8, 2004 entitled "OPEN VESSEL SEALING INSTRUMENT WITH CUTTING MECHANISM AND DISTAL LOCKOUT".

In addition, the presently disclosed forceps may include an electrical cutting configuration to separate the tissue either prior to, during or after cutting. One such electrical configuration is disclosed in commonly-assigned U.S. patent application Ser. No. 10/932,612 entitled "VESSEL SEALING INSTRUMENT WITH ELECTRICAL CUTTING MECHANISM," which is herein incorporated by reference.

Moreover, only one sensor in one jaw member may be utilized to measure the initial and real-time changes in the gap distance "G." The sensor may be configured to provide an initial gap distance value to the microprocessor or generator, which enables a predetermined starting gap distance value, trajectory and ending gap distance value.

In addition, the gap distance "G" may be selectively regulated by adjusting one or more stop members that extend from the tissue sealing surfaces. Several configurations of this feature are shown in a commonly-owned U.S. patent application Ser. No. 10/846,262 entitled "TISSUE SEALER WITH NON_CONDUCTIVE VARIABLE STOP MEMBERS AND METHOD OF SEALING TISSUE," which is herein incorporated by reference.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A method for sealing tissue comprising the steps of: providing an electrosurgical forceps having a drive rod and an end effector assembly coupled to the drive rod at a distal end thereof, the end effector assembly including jaw members wherein longitudinal reciprocation of the drive rod moves the jaw members from a first position in spaced relation relative to one another to at least one subsequent position wherein the jaw members cooperate to grasp tissue therebetween; providing a pressure applicator coupled to the drive rod; grasping tissue between sealing plates associated with the jaw members; sensing a gap distance between the sealing plates; and controlling the pressure applicator in response to the sensed gap distance in order to reciprocate the drive rod.

2. A method as in claim 1, further comprising the step of generating a desired gap distance trajectory based on an initial gap distance, wherein the desired gap distance trajectory includes a plurality of desired target gap distance values.

3. A method as in claim 2, wherein the step of generating the desired gap trajectory further includes substantially matching the sensed gap distance to a corresponding desired target gap distance value.

4. A method as in claim 1, wherein the step of sensing the gap distance between the sealing plates comprises sensing the gap distance between the sealing plates through at least one sensor selected from the group consisting of a laser distancer, an LED distancer and an optical encoder.

5. A method as in claim 1, wherein the pressure applicator is selected from the group consisting of an electrical motor, a linear actuator, a pneumatic cylinder and a hydraulic cylinder.

6. A method as in claim 1, further comprising the step of determining at least one pre-surgical tissue parameter and transmitting data pertaining to the at least one pre-surgical tissue parameter to a controller.

7. A method as in claim 6, wherein the step of determining at least one pre-surgical tissue parameter further includes selecting the least one pre-surgical tissue parameter from the group consisting of boundary conditions, jaw fill and hydration.

8. A method as in claim 1, wherein the step of controlling the pressure applicator further comprises controlling the pressure applicator as a function of the at least one pre-surgical tissue parameter during the sealing process.

* * * * *